US011181517B2

(12) United States Patent
McPeek

(10) Patent No.: US 11,181,517 B2
(45) Date of Patent: *Nov. 23, 2021

(54) SYSTEMS AND METHODS FOR MONITORING AGRICULTURAL PRODUCTS

(71) Applicant: AGERpoint, Inc., New Smyrna Beach, FL (US)

(72) Inventor: K. Thomas McPeek, Orlando, FL (US)

(73) Assignee: AGERPOINT, INC., New Smyrna Beach, FL (US)

(*) Notice: Subject to any disclaimer, the term of this patent is extended or adjusted under 35 U.S.C. 154(b) by 97 days.

This patent is subject to a terminal disclaimer.

(21) Appl. No.: 16/707,198

(22) Filed: Dec. 9, 2019

(65) Prior Publication Data

US 2020/0132651 A1    Apr. 30, 2020

Related U.S. Application Data

(63) Continuation of application No. 15/977,771, filed on May 11, 2018, now Pat. No. 10,520,482, which is a continuation-in-part of application No. 15/868,840, filed on Jan. 11, 2018, now Pat. No. 10,371,683, which is a continuation of application No. 13/907,147, filed on May 31, 2013, now Pat. No. 9,939,417.

(60) Provisional application No. 61/654,312, filed on Jun. 1, 2012.

(51) Int. Cl.
| G01N 33/00 | (2006.01) |
| G01N 21/25 | (2006.01) |
| G01B 5/00 | (2006.01) |
| G01N 33/02 | (2006.01) |
| G01N 21/84 | (2006.01) |
| G01N 21/17 | (2006.01) |
| G01B 11/24 | (2006.01) |

(52) U.S. Cl.
CPC ....... *G01N 33/0098* (2013.01); *G01B 5/0035* (2013.01); *G01N 21/251* (2013.01); *G01N 33/025* (2013.01); *G01B 11/24* (2013.01); *G01N 2021/1797* (2013.01); *G01N 2021/8466* (2013.01)

(58) Field of Classification Search
CPC .... G01N 21/31; G01N 21/251; G01N 33/025; G01N 33/0098; G01N 2021/8466; G01N 2201/0216; G01N 2021/1797; G01N 21/359; G01B 5/0035; G01B 11/24
See application file for complete search history.

(56) References Cited

U.S. PATENT DOCUMENTS

| 6,862,083 B1* | 3/2005 | McConnell, Sr .... A01B 79/005 356/4.01 |
| 2008/0074640 A1* | 3/2008 | Walsh .................. G01S 7/4818 356/5.01 |

* cited by examiner

*Primary Examiner* — Yoshihisa Ishizuka
(74) *Attorney, Agent, or Firm* — Bryan Cave Leighton Paisner LLP

(57) ABSTRACT

The present invention relates to systems and methods for monitoring agricultural products. In particular, the present invention relates to monitoring fruit production, plant growth, and plant vitality. According to embodiments of the invention, a plant analysis system is configured determine a spectral signature of a plant based on spectral data, and plant color based on photographic data. The spectral signatures and plant color are associated with assembled point cloud data. Morphological data of the plant can be generated based on the assembled point cloud data. A record of the plant can be created that associates the plant with the spectral signature, plant color, spectral data, assembled point cloud data, and morphological data, and stored in a library.

20 Claims, 14 Drawing Sheets

Figure 2

| TASK TYPE 1 | Determine diameter and/or circumference of the trunk of each tree<br>Determine the overall height of each tree<br>Determine the overall volume of each tree<br>Determine the leaf density of each tree<br>Determine average leaf color of each tree | TOOL 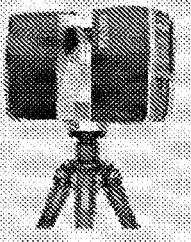 |
|---|---|---|
| TASK TYPE 2 | Determine the GPS location of each tree<br>Attach a unique RFID - Barcode identifier to each tree | TOOL  |
| TASK TYPE 3 | Determine the predicted yield from blossom and fruit | TOOL  |
| TASK TYPE 4 | Seamlessly connect to existing industry standard software solutions for tracking grove operations and harvest control | TOOL 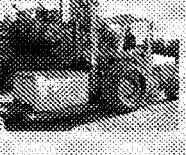 |

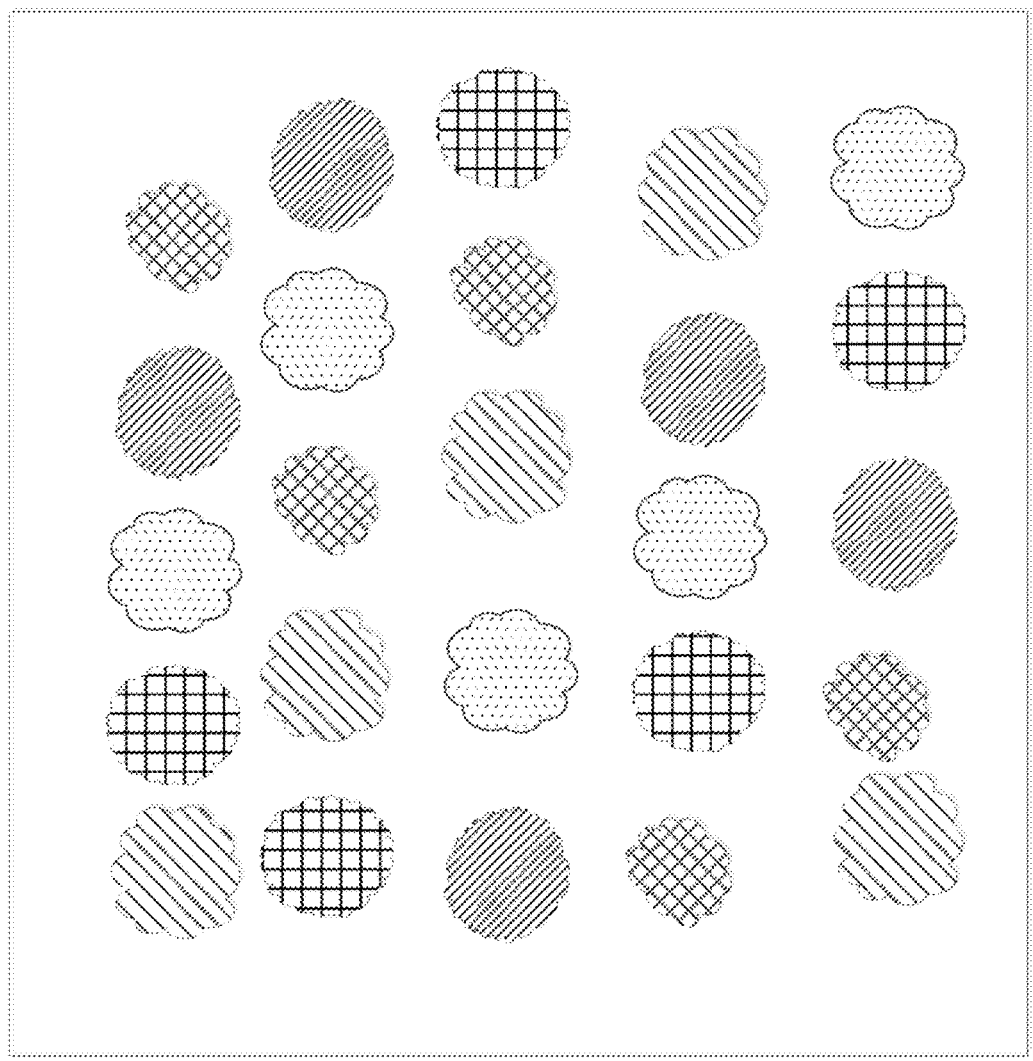
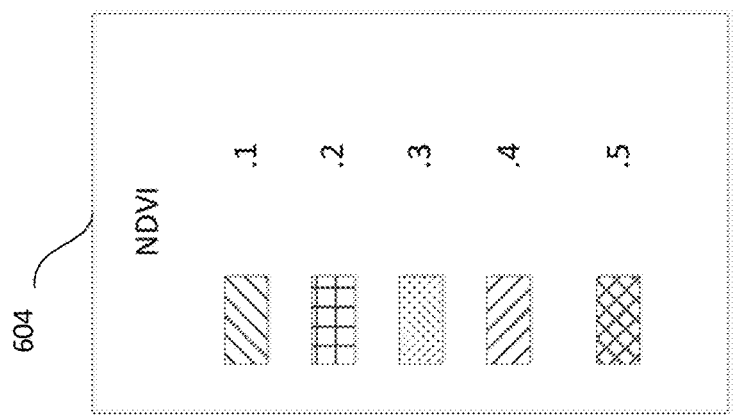
Figure 6c

SYSTEMS AND METHODS FOR MONITORING AGRICULTURAL PRODUCTS

CROSS REFERENCE TO RELATED APPLICATIONS

This application is a continuation application of, and claims the benefit of, of U.S. patent application Ser. No. 15/977,771 filed on May 11, 2018, which is a continuation-in-part application of, and claims the benefit of, and priority to, U.S. patent application Ser. No. 15/868,840 filed on Jan. 11, 2018 (issued as U.S. Pat. No. 10,371,683), which claims priority to U.S. patent application Ser. No. 13/907,147 filed on May 31, 2013 (issued as U.S. Pat. No. 9,939,417), which claims priority to U.S. Provisional Patent Application No. 61/654,312, filed Jun. 1, 2012, each of which are hereby incorporated by reference in their entirety as if recited in full herein.

FIELD OF THE INVENTION

The present invention relates to systems and methods for monitoring agricultural products. In particular, the present invention relates to agricultural asset management, including: monitoring fruit production, tracking plant growth, monitoring plant vitality and productivity, measuring morphological attributes and performing field-based phenotyping.

BACKGROUND OF THE INVENTION

Accurate and timely machine counting of fruit on the tree or vine has long been considered impossible or impractical. Current methods rely on manual estimation and are often inaccurate and labor intensive. Inaccurate estimates lead to inaccurate crop forecasts. This inaccuracy complicates pricing and grower's ability to forecast plan, and optimize market timing participation. What is needed is an improved method for accurately determining and forecasting plant size and quality and harvested yield.

Further, agricultural systems typically do not take into account how the genetics of a plant can impact properties such as size and quality based on observed phenotypical data.

SUMMARY OF THE INVENTION

The present invention relates to systems and methods for monitoring agricultural products. In particular, the present invention relates to monitoring fruit production, plant growth, and plant vitality.

Embodiments of the present disclosure provide systems and methods for improved fruit tree analysis and crop predictions. The systems and methods described herein improve on the accuracy and efficiency of existing methods. The systems and methods of embodiments of the present invention find use in research, commercial agriculture, and forestry, among other uses.

For example, in some embodiments, the present invention provides an analysis system, comprising: a) a data acquisition component; b) optionally, a transport component configured to transport the data acquisition component to collect data on fruit trees or vines; and c) a software component configured to analyze the data to generate analyzed data. In some embodiments, the transport component is a transport vehicle, The transport vehicle may be a four-wheel independent suspension engine for transporting one or more sensors over an uneven terrain with minimal noise. The transport vehicle may have a cargo box for storing and supporting modular sensor mounts and fixtures. The cargo box may be formed with a high-density polyethylene copolymer composite material that eliminates rust, dents, and reduces noise.

In some embodiments, the transport vehicle is autonomous or remotely controlled. The transport vehicle can be autonomously controlled based on assembled point cloud data to navigate around and through one or more plants. For example, assembled point cloud data of an orchard, including the precise position of each plant in the orchard, can be stored on the transport vehicle. The transport vehicle can then navigate through the orchard, and based on its current position as determined by the global navigation satellite system, and the location of that position relative to the assembled point cloud, the transport vehicle can detect plants in its proximity and/or path and avoid colliding with the plants.

In some embodiments, the data acquisition component comprises one or more devices selected from, for example, one or more of a 3D laser scanner, a survey grade GPS, thermal imaging, radio, sound and magnetic waves, a thermal imaging camera, multispectral and/or hyperspectral sensors, soil conductivity sensors or a high-speed, high-density (HD) video camera. In some embodiments, the data may include, for example, one or more of tree trunk diameter, height of tree, volume of tree, leaf density of tree, color of leaves on tree, GPS location of tree, bar code data for tree, number of blossoms on tree, presence of pests including diseases on the fruit or tree, subspecies of the tree, or an annotated or un-annotated photograph of the tree. In some embodiments a full three-dimensional virtual representation of the tree is produced at sub-centimeter-level resolution.

The present invention is not limited to the analysis of a particular fruit tree or vine. Plants that can be analyzed by embodiments of the invention can include without limitation permanent crop plants, crop trees, forestry, and corn. Examples include but are not limited to, abiu, acerola, almond, amla (indian gooseberry), apple, apricot, aprium, avocados, bael, bananas, ber (indian plum), blackberries, blood orange, blueberries, breadfruit, calamondin, cantaloupe melon, carambola (starfruit), cashew, the fruit, cherries, chestnut, chocolate, chokecherry, citron, cocoa, coconuts, coffee, corn plant, crabapple, cumaquat, currant, custard-apple, dates, dewberries, dragon fruit, durian, feijoa, fig, grapefruit, grapes, guava, hazelnut, honeydew, hops, jaboticaba, jackfruit, jujube, kaffir lime, key lime, kiwifruit, kumquat, lemons, limes, loganberries, longan, loquat, lychee, macadamia, mandarin, mangoes, mangosteen, medlar, morello cherry, mulberries, natal plum, nectarines, oil palm, olives, oranges, papayas, passion fruit, pawpaw, peaches, pears, pecan, persimmon, pineapples, plums, pluot, pomegranate, pomelo, pongamia, prune, pummel, pumpkin, raspberries, red banana, rock melon, sabine, sapodilla (chikoo), sapote, soursop, starfruit, stone fruit, strawberries, strawberry tree, sugar-apple (sharifa), surinam cherry, tamarillo, tamarind, tangelos, tangerines, tomatoes, ugli, uglifruit/uniqfruit, walnut, watermelon, a grape vine, a tomato vine, or an apple tree.

In some embodiments, the software component further comprises a computer processor and a user interface configured to provide or display the analyzed data (e.g., to a user). In some embodiments, the analyzed data may represent, for example, one or more of tree health, predicted fruit yield, predicted fruit ripening period, or other features of interest.

In further embodiments, the present invention provides a method, comprising: a) collecting data on plants (e.g., fruit trees) using a data acquisition component transported by a transport component; and b) analyzing the data with a software component to generate analyzed data. In some embodiments, the method further comprises the step of using the analyzed data to calculate spray dispersal and/or in order to guide fruit tree sprayers (e.g., to determine when to spray, how long to spray, and what chemicals to spray). In some embodiments, the method further comprises the step of identifying species and/or subspecies of the tree. In some embodiments, the method further comprises the step of identifying disease in the tree and/or fruit.

In some embodiments, the invention may comprise a plant analysis system that includes a 3D laser scanner, a camera, a spectral sensor, and a survey grade global positioning satellite (GPS) receiver. The survey grade GPS receiver can be configured to measure location with a sub centimeter level of accuracy. The 3D laser scanner can be configured to measure properties of a plant utilizing light detection and ranging (LiDAR), including waveform LiDAR and assemble point cloud data. Assembled point cloud data can include three dimensional vertices, each of which represents the external surface of an object on the plant. The camera can collect photographic data of the plant, the spectral sensor can gather spectral data of the plant, and the GPS receiver can geo-register the point cloud data and the photographic data. In some aspects of the invention, the system can fuse the data collected from the plant analysis system to enable the generation of morphological and phenotypical data for further analysis. Each three dimensional vertex of the assembled point cloud data can be associated with GPS data, photographic data, and spectral data.

The plant analysis system can include a transport vehicle that can transport the 3D laser scanner, camera, spectral sensor, and survey grade GPS receiver to collect the data on the plant. The transport vehicle can be a manned or unmanned, ground-based or airborne vehicle for transporting the plant analysis system. In some embodiments, the spectral sensor can be an active hyperspectral sensor. The plant analysis system can include a computer processor configured to determine a spectral signature of the plant based on the spectral data. The computer processor can also be configured to determine plant color based on photographic data and associate the assembled point cloud data with the plant color. The computer processor can further generate morphological data of the plant based on the assembled point cloud data, the morphological data comprising plant stem diameter, plant height, plant volume, and plant leaf density. The computer processor can create a record of the plant in a library. The record of the plant associates the plant with the spectral signature, the plant color, the spectral data, the assembled point cloud data, and the morphological data.

In some embodiments, the computer processor of the plant analysis system can generate morphological data by segmenting the assembled point cloud data to identify boundaries of the plant. The computer processor can classify the morphological data to identify a plant feature. The plant feature can include a branching structure, trunk, biomass, canopy, fruit, blossom, fruit cluster, or blossom cluster.

In some embodiments, the computer processor of the plant analysis system can utilize the assembled point cloud data and the plant color to discriminate a fruit, blossom, fruit cluster, or blossom cluster from a shadow. The discrimination can be based on analyzing a pixel-by-pixel variation of the plant color and a geometric shape defined by the vertices of the assembled point cloud data.

In some embodiments, the plant analysis system can further include atmospheric sensors for measuring atmospheric conditions. The computer processor can determine a phenotype of a plant based on the spectral signatures, morphological data, and atmospheric conditions measured by the atmospheric sensors.

In some embodiments, the computer processor of the plant analysis system can be configured to determine a vegetation index of one or more plants based on the spectral data. In yet other embodiments, the computer processor of the plant analysis system can be configured to determine a number and a size of fruits or blossoms on a plant. The number and size of fruits or blossoms on a plant can be based on a fusion of the assembled point cloud data and plant color data. The number and size of fruits or blossoms on a plant can be determined by clustering the assembled point cloud data and plant color data. The number and size of fruits or blossoms on a plant can be used to calculate a crop yield estimate. In some embodiments, additional data, such as spectral data, can be fused to enhance the counting and sizing of fruits or blossoms.

In some embodiments, the computer processor of the plant analysis system can be configured to compare a spectral signature of a plant with a spectral signature from the library of plant records based on the spectral information divergence of the spectral signatures. The computer processor can be further configured to detect the presence of a plant disease based on the comparison of spectral signatures and image analysis. The computer processor can also be configured to detect the presence of wilt or leaf drop caused by environmental stressors based on the comparison of spectral signatures, point clouds, and image analysis. The computer processor can also be configured to identify a disease vector and predict the disease vector's trajectory. In some embodiments, the library of plant records is configured to store historical data associated with a plant. The historical data can include information such as the date of planting, root stock, grafting record, nutritional treatment, health treatment, yield, surrounding soil conditions, surrounding atmospheric conditions, and surrounding topography. In some embodiments, the plant analysis system can further include an asset management dashboard for accessing, viewing, analyzing and controlling the library of plant records.

Additional embodiments are described herein.

DESCRIPTION OF THE FIGURES

FIG. 2 shows a task-methodology breakdown of systems and methods of embodiments of the present invention.

FIGS. 6a, 6b, and 6c show an asset management dashboard according to some embodiments of the invention.

DEFINITIONS

Figure 1:
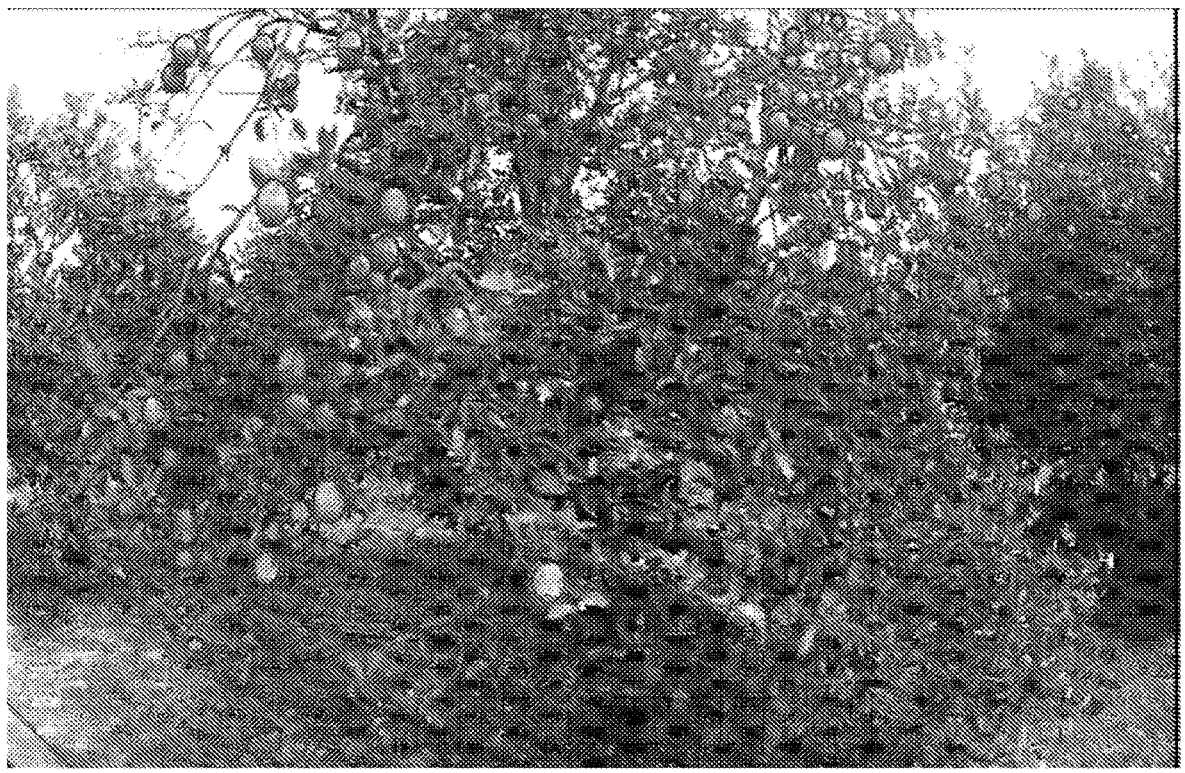
FIG. 1 shows an image of annotations of trees generated by systems and methods of embodiments of the present invention.
Figure 3:
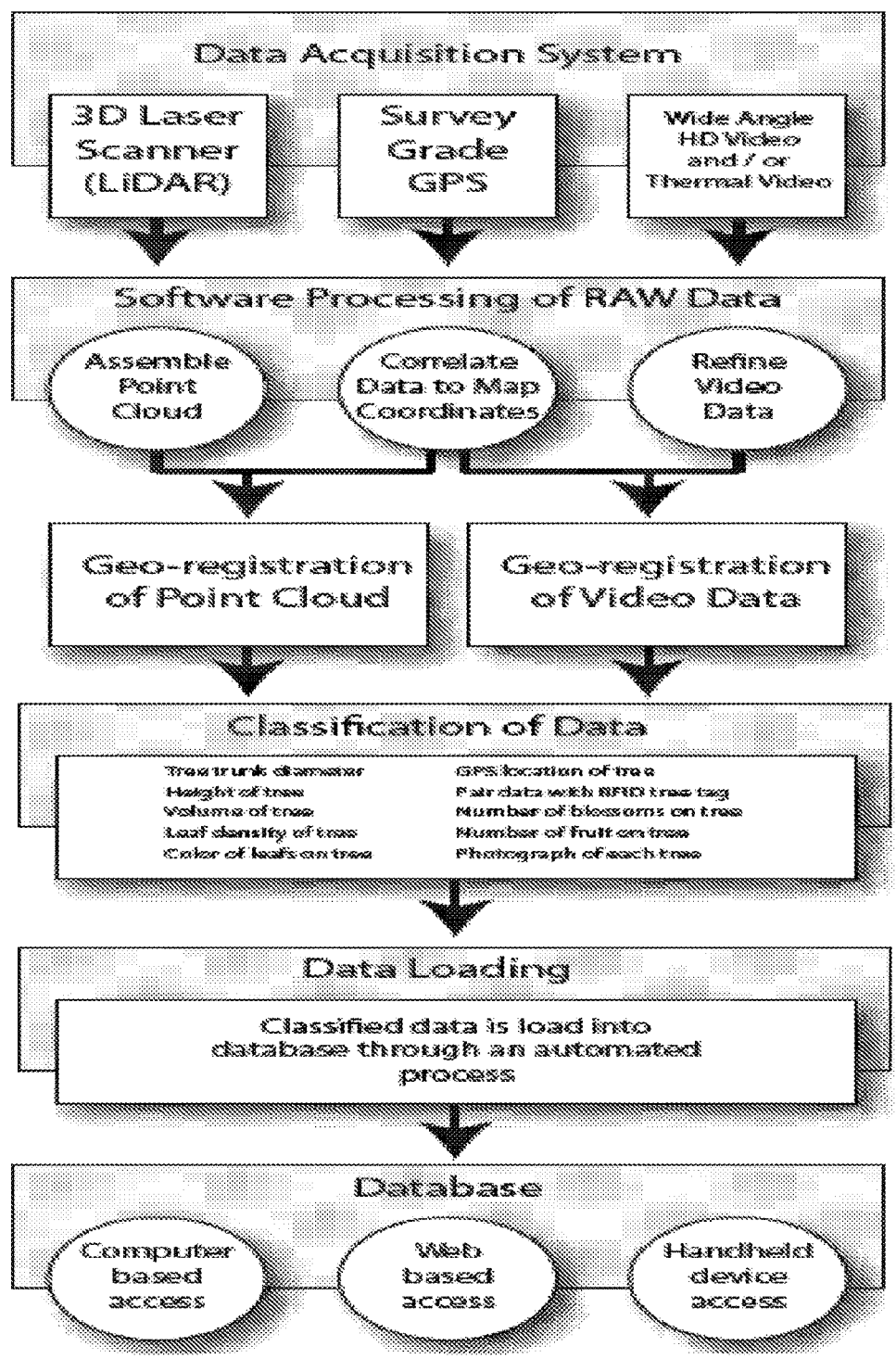
FIG. 3 shows a schematic of an exemplary crop analysis system for fruit bearing trees and vine crops.
Figure 4:
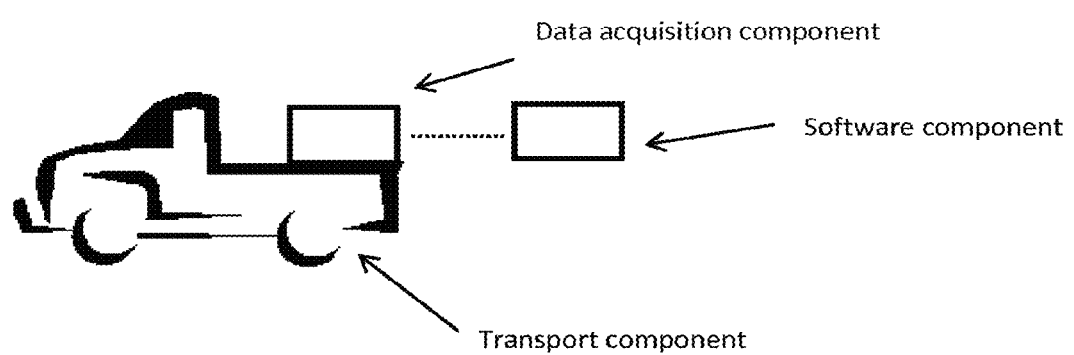
FIG. 4 shows a schematic of an exemplary crop analysis system for fruit bearing trees and vine crops.

To facilitate understanding of the invention, a number of terms are defined below.

As used herein, the terms "processor" and "central processing unit" or "CPU" are used interchangeably and refer to a device that is able to read a program from a computer memory (e.g., ROM or other computer memory) and perform a set of steps according to the program.

As used herein, the terms "computer memory" and "computer memory device" refer to any storage media readable by a computer processor. Examples of computer memory include, but are not limited to, random access memory (RAM), read only memory (ROM), computer chips, digital video discs (DVD), compact discs (CDs), hard disk drives (HDD), and magnetic tape.

As used herein, the term "computer readable medium" refers to any device or system for storing and providing non-transitory information (e.g., data and instructions) to a computer processor. Examples of computer readable media include, but are not limited to, DVDs, CDs, hard disk drives, magnetic tape and servers for streaming media over networks.

As used herein, the term "in electronic communication" refers to electrical devices (e.g., computers, processors, etc.) that are configured to communicate with one another through direct or indirect signaling.

As used herein, the term "survey grade GPS" refers to global positioning satellite (GPS) receivers that are able to map locations with a very high degree of accuracy. For example, in some embodiments, survey grade GPS receivers can measure an object's absolute position on the earth to within 1 centimeter (0.4 inches) or lower.

As used herein, the term "fruit tree" refers to any perennial tree, bush, or vine that produces a fruit. The term "fruit" refers to a part of a flowering plant that derives from specific tissues of the flower and is not limited to culinary fruits. Examples include but are not limited to, abiu, acerola, almond, amla (indian gooseberry), apple, apricot, aprium, avocados, bael, bananas, ber (indian plum), blackberries, blood orange, blueberries, breadfruit, calamondin, cantaloupe melon, carambola (starfruit), cashew, the fruit, cherries, chestnut, chocolate, chokecherry, citron, cocoa, coconuts, coffee, corn plant, crabapple, cumaquat, currant, custard-apple, dates, dewberries, dragon fruit, durian, feijoa, fig, grapefruit, grapes, guava, hazelnut, honeydew, hops, jaboticaba, jackfruit, jujube, kaffir lime, key lime, kiwifruit, kumquat, lemons, limes, loganberries, longan, loquat, lychee, macadamia, mandarin, mangoes, mangosteen, medlar, morello cherry, mulberries, natal plum, nectarines, olives, oil palm, oranges, papayas, passion fruit, pawpaw, peaches, pears, pecan, persimmon, pineapples, plums, pluot, pomegranate, pomelo, pongamia, prune, pummel, pumpkin, raspberries, red banana, rock melon, sabine, sapodilla (chikoo), sapote, soursop, starfruit, stone fruit, strawberries, strawberry tree, sugar-apple (sharifa), surinam cherry, tamarillo, tamarind, tangelos, tangerines, tomatoes, ugli, uglifruit/uniqfruit, walnut, watermelon, a grape vine, a tomato vine, or an apple tree. In some embodiments, the fruit tree is a citrus tree (e.g., those described above).

DETAILED DESCRIPTION OF THE INVENTION

The present invention relates to systems and methods for monitoring agricultural products. In particular, the present invention relates to agricultural asset management, including: monitoring fruit production, tracking plant growth, monitoring plant vitality and productivity, measuring morphological attributes and performing field-based phenotyping. By fusing data collected by a data acquisition component and software component, embodiments of the present invention provide systems and methods for performing the foregoing.

The ability to accurately predict fruit yield and quality in advance of harvest provides a significant advance for growers in the fruit industry. The systems and methods of embodiments of the present invention provide an accurate inventory of crop holdings, including the images and geolocation of each plant, as well as providing three dimensional models in the form of point clouds for data dissemination. In some embodiments the models can also be polygon models.

Embodiments of the present invention provide systems and methods for assessing agricultural crops (e.g., fruit trees, bushes, or vines). The systems and methods described herein find use in a variety of applications (e.g., providing information to companies engaged in growing fruit crops, those insuring fruit crops and those who invest in agricultural commodities).

In one aspect of the invention, the system is adaptable to monitor the physical attributes of a wide variety of different species of fruiting plants, or different subspecies of fruiting plants. For example, because some plant varieties or cultivars are taller than other varieties, the system may be adapted and scaled to scan and collect data from trees and vines that have vast differences in height within the same row or column or region of an orchard. In preferred embodiments, the LiDAR sensor is positioned approximately 1.5-3 meters from the surface of the ground to provide desirable range accuracy. In some embodiments of the invention, the LiDAR scanner is a push-broom scanner that collects data through an array of detectors that are perpendicular to the direction of travel. In this way, the system may generate and geo-register point cloud data on a moving platform.

In some embodiments of the invention, the point cloud data may be used to form a digital elevation model to accurately and precisely determine not only a tree's morphology, but also, the lay of the land. For example, the point cloud data may be used to calculate a tree's canopy height by determining the distance between vertices representing the ground and vertices representing the tree's canopy crown.

The present invention is not limited to a particular fruit tree or vine. Plants that can be analyzed by using the systems and methods described herein can include without limitation permanent crop plants, crop trees, forestry and fruit bearing plants. Examples of fruit bearing plants include but are not limited to abiu, acerola, almond, amla (indian gooseberry), apple, apricot, aprium, avocados, bael, bananas, ber (indian plum), blackberries, blood orange, blueberries, breadfruit, calamondin, cantaloupe melon, carambola (starfruit), cashew, the fruit, cherries, chestnut, chocolate, chokecherry, citron, cocoa, coconuts, coffee, corn plant, crabapple, cumaquat, currant, custard-apple, dates, dewberries, dragon fruit, durian, feijoa, fig, grapefruit, grapes, guava, hazelnut, honeydew, hops, jaboticaba, jackfruit, jujube, kaffir lime, key lime, kiwifruit, kumquat, lemons, limes, loganberries, longan, loquat, lychee, macadamia, mandarin, mangoes, mangosteen, medlar, morello cherry, mulberries, natal plum, nectarines, oil palm, olives, oranges, papayas, passion fruit, pawpaw, peaches, pears, pecan, persimmon, pineapples, plums, pluot, pomegranate, pomelo, pongamia, prune, pummel, pumpkin, raspberries, red banana, rock melon, sabine, sapodilla (chikoo), sapote, soursop, starfruit, stone fruit, strawberries, strawberry tree, sugar-apple (sharifa), surinam cherry, tamarillo, tamarind, tangelos, tangerines, tomatoes, ugli, uglifruit/uniqfruit, walnut, watermelon, a grape vine, a tomato vine, or an apple tree. In some embodiments, the fruit tree is a citrus tree (e.g., those described above).

Permanent crop plants include without limitation trees, bushes or vines that, once planted, produce agricultural products that can be harvested repeatedly over multiple growing seasons. Permanent crop plants can be used to create products that include leaves and bark, such as for example tea, cinnamon, cork and similar crops. They can also be used to create saps and other liquid crops, from plants such as sugar maple, birch, palm tree and other similar crops. Permanent crops can include fruiting trees, such as for example apple trees, pear trees, fig trees, olive trees, and banana trees; citrus trees such as for example, orange trees, lemon trees, and grapefruit trees; stone fruit trees, such as for example peach trees, avocado trees, and cherry trees; nut trees such as for example pecan trees, walnut trees, and almond trees; and berry bushes, such as for example, blueberry bushes, raspberry bushes, and other similar crops. Permanent crops can also include vines, which can include, but are not limited to, table grapes, wine grapes, kiwi, and other similar crops.

Crop trees include trees that are harvested in total, one time, but take multiple seasons of growth prior to harvest. These can produce such diverse agricultural products as pulp for paper, lumber, and decorative uses such as Christmas trees and other similar uses.

In some embodiments, the present invention provides systems and methods for a) determining the diameter and/or circumference of a tree trunk or vine stem, determining the overall height of each tree or vine, determining the overall volume of each tree or vine, determining the leaf density and leaf color of each tree or vine; b) determining the GPS location of each plant and attaching a unique identifier (e.g., RFID tag or barcode identifier) to each plant or vine; c) determining the predicted yield from identified morphology blossoms and/or fruit; and d) providing yield and harvest date predictions or other information to end users using a user interface. In some embodiments, the technology is used to size fruit while it is still on the tree (e.g., for applications where selective harvest is done based on size).

Embodiments of the present invention provide a variety of hardware and software systems to perform the described methods. In some embodiments, systems comprise one or more (e.g., all) the following components: survey grade GPS, 3D laser scanners, static and motion imaging (e.g., RGB, multi-spectral, hyper-spectral, NWIR and SWIR), high speed HD video, transport vehicles, computer software, computer processors, and user interfaces.

The global positioning system (GPS) is a space-based satellite navigation system that provides location and time information in all weather, anywhere on or near the Earth, where there is an unobstructed line of sight to four or more GPS satellites. GPS systems generally fall in one of four categories of accuracy, sub-centimeter (0.39370 inch), sub decimeter (3.937 inches), sub meter (39.37 inches), and sub decameter (32.8 feet). In some embodiments, survey grade GPS (e.g., sub centimeter) is used to locate fruit, and trees or vines to high levels of detail. Survey grade GPS receivers determine location to very high accuracy (e.g., 1 inch or less, 1 centimeter or less, etc.). GPS is a type of global navigation satellite system (GNSS). The GNSS in Russia is GloNASS, and the GNSS in China is known as BEIDOU.

In some embodiments, commercially available equipment is utilized. For example, survey grade GPS receivers are available from a variety of suppliers (e.g., Igage Mapping Corporation, Salt Lake City, Utah; Hemisphere Inc., Calgary, Alberta, Canada; Trimble Navigation Limited, Sunnyvale, Calif.).

In some embodiments, the systems and methods may include an inertial navigation system (INS) to calculate sensor motion and orientation. An INS may include one or more inertial measurement units (IMUs), which may comprise accelerometers, gyroscopes, and magnetometers for providing relative measurements of motion and orientation, such as for example, roll, pitch, or yaw. The motion and orientation measurements may be used to improve the location measured by the data acquisition component. In turn, the improved position measurements may be used to improve the mapping of the point cloud data into geographic space. The INS additionally provides tracking when satellite communications become unavailable, such as for example, when the equipment is under a tree canopy or similar obstruction.

In some embodiments of the invention, the INS may be coupled to or include a GNSS receiver. In this way, the INS may determine an initial position, orientation, and velocity. As the transport component travels through an orchard, its acceleration, orientation, and velocity may be measured by the INS and used to extrapolate its position based on the initial position, orientation and velocity measurements. For example, if the GPS loses its signal with a satellite, the position of the transport component may be estimated based on the acceleration, orientation, and velocity measurements recorded by the INS.

In some embodiments of the invention, the position data measured by the INS and GPS may be processed for errors. For example, after the transport component has gathered data, the data recorded by the GPS or INS may be analyzed to determine if there was an error in the GPS data (e.g., because of a canopy obstructing the signal to a GPS satellite). Errors may be identified by comparing the GPS data to the INS data (which may include data obtained from the IMU such as roll, pitch, or yaw data, or any combination thereof). If the GPS data suggests that the trajectory of the transport vehicle shifted in one direction, yet the IMU data suggests the trajectory of the transport component did not change based on its measured yaw, it may be determined that the position of the transport vehicle is more accurately reflected by the readings of the IMU. The position of the transport vehicle may then be determined by generating a smooth best estimate trajectory ("SBET"), which is described in more detail below.

In some embodiments of the invention, the INS and GPS may be integrated together, and may further include a second IMU integrated into the circuitry of the GPS. The second IMU may then be used to correct the GPS calculations in the same manner as described above, and in real-time. The second IMU may measure physical movements of the device in at least 3 axes, including pitch, yaw, and roll. The yaw axis measurement may be used to compensate for GPS signal outages or position errors. When traveling down a substantially straight trajectory, such as for example when traveling through a row, the inertial navigation system may use the yaw axis measurement data to project the path of the collection vehicle along the same substantially straight trajectory it was previously traveling on. In this way, the IMU data is used to smooth the position outliers by assuming the transport vehicle continued to travel along the same substantially straight trajectory it was previously traveling on. In other embodiments of the invention, different trajectories may be modeled using information known about the orchard or the route or path the transport vehicle planned to take. For example, knowledge of the layout of the orchard may include the geometry of the rows formed in the orchard. The layout of the circular or spiraled rows, may then be used to model circular or spiraled trajectories of the transport vehicle. Similarly, knowledge of what path the transport vehicle is planned to take in an orchard may be used to extrapolate the transport vehicle's trajectory path.

In other embodiments of the invention, the INS further comprises a base receiver station positioned in a fixed location proximal to the orchard. While the INS travels through the orchard, the INS may receive messages from a GPS satellite which it may forward to the base station. In this way, the INS functions similarly to a rover station in a real-time kinematic positioning system. While the INS transmits messages to the base station, the base station in parallel receives the same messages from the GPS satellite. Thus, the base station receives messages from the GPS satellite in sync with the INS. The base station may then compare the GPS message received directly from the GPS satellite to the GPS message received from the INS. Based on this comparison, the base station may determine whether the transport vehicle has deviated from a trajectory path based on its GPS data, and thus if there have been any anomalies or errors with the INS. The messages the base station receives from the GPS satellite describe the orbital information (ephemeris) of the satellites in view and the pseudo-range data (observables or epochs) describing the position of the other satellites in the GNSS with respect to the position of the base station. The base station will reliably know the geometry of the satellites because it will have a constant viewing point to them. As such, it is enabled to provide reliable position corrections to the rover when the rover has an outage or cycle slip.

In some embodiments of the invention, the orbits or position of the satellites may be used to improve the accuracy of the data. Specifically, the precise ephemeris files which describe the exact orbit and position information of the satellites may be downloaded. The exact orbit and position information may then give precise position measurements, improving positional accuracies to as little as a few centimeters. Having high accuracy at the resolution of centimeters enables the system to fuse sensor data and positional data with a high degree of precision and accuracy. Further, errors that occur during real-time collection may be corrected, eliminating bias from poor satellite coverage.

In some embodiments of the invention, when the base station determines that there has been a deviation, the base station may then compare the GPS data of the transport vehicle to the GPS data received directly from the GPS satellite. If the GPS data received directly from the GPS satellite suggests a different trajectory path, it may be determined that the GPS data of the inertial navigation system is inaccurate. A SBET may then be generated to correct for the deviation, as described in more detail below.

In some embodiments of the invention, the software component may use a weighting system for the positional data sources when generating the SBET. Specifically, if one positional data source is consistently unreliable, the software component may give that positional data source less weight when creating a SBET. For example, one GPS satellite may be causing a bias to the positional data. Knowing that the particular GPS satellite is causing a bias, the software component may correct for that bias by according that satellite less weight when calculating a geodetic position.

A SBET may be created by performing a series of filtering algorithms on the geodetic positional data calculated by the INS and GPS. For example, in some embodiments of the invention, the software component may apply a Kalman filter to the geodetic positional data measured by the INS. It may then continue to filter the geodetic positional data by applying a forward, reverse, combine, precise forward, and then smoothing correction filter to the geodetic positional data, resulting in a SBET. Whereas the original/raw geodetic positional data may be accurate to about 10 meters during a collection, in some aspects of the invention, the improved error identification and correction processes described above allow the INS to achieve a resolution of geodetic position data as low as 1-3 centimeters in both the horizontal and vertical axes, and as low as millimeters in the horizontal axis.

The processing of the position data described above may be performed by the software component or data acquisition component, in real-time or after the data has been collected. However, according to some embodiments of the invention shown in FIG. 9, the system may include a post-processing server 901 that performs the processing of the position data. The post-processing server 901 may receive position data from one or more software components or data acquisition components 903 coupled to or mounted on one or more transport vehicles 904. The post-processing server 901 may then provide the post-processed data to one or more asset management dashboards 902. The post-processing server 901 may also process any other data collected, generated, or processed by the data acquisition component and computer processor coupled to the transport vehicle.

Figure 5:
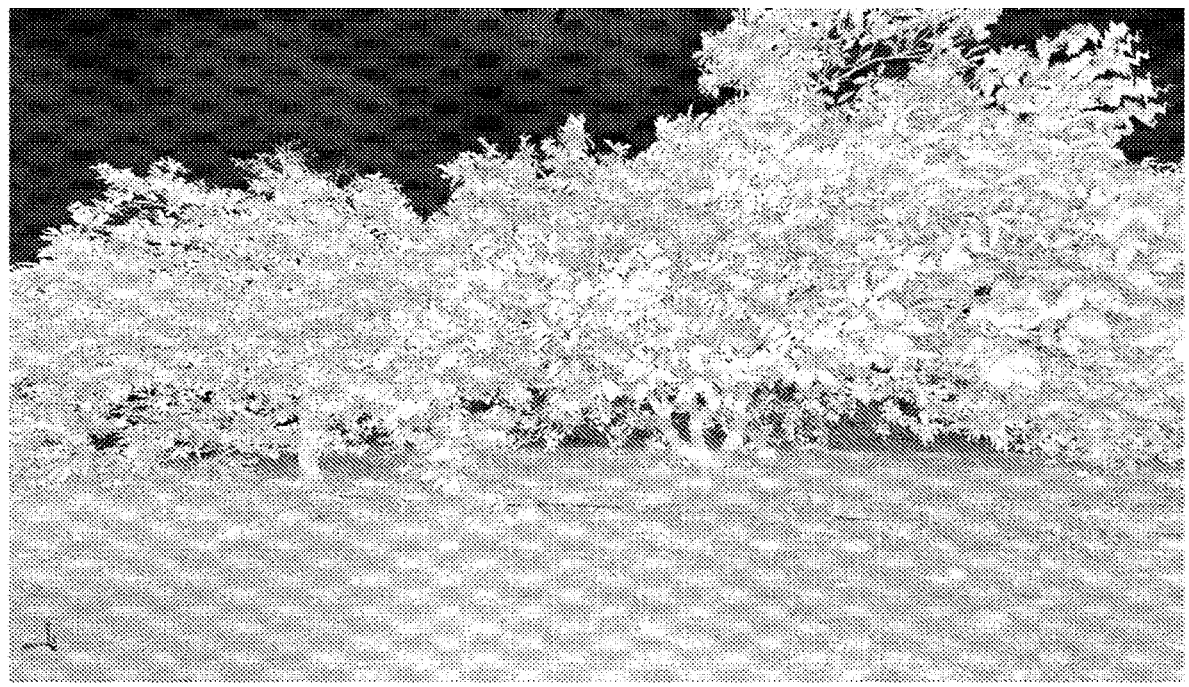
FIG. 5 shows an example of a point cloud map of a fruit tree.

Each position measured by the GPS and INS may be recorded and associated with a time stamp. As explained in more detail below, the time stamp may then be used to fuse data measured by other sensors of the system. In some embodiments, 3D laser scanners are utilized to map fruit or tree or vine properties. The term "3D scanner" is a colloquial term used to describe a device used for light detection and ranging (LiDAR) which is an optical remote sensing technology that can measure the distance to, or other properties of a target by illuminating the target with light. LiDAR can be found in two common forms direct energy detection, also known as incoherent, and coherent detection. Coherent systems are typically preferred for measurement systems. Both systems are currently available in two pulse formats: micropulse and high-energy systems. The micropulse systems are eyesafe and require less energy to operate but this comes at the expense of higher computational post-processing requirements. Some LiDAR systems currently in use are capable of collecting nearly one million points per second. The data collected is represented as a point cloud as demonstrated in FIG. 5. In a point cloud, the individual points model the surface of every object in the sensor's range. For example, the point cloud may be parsed into models of leaves, branches, fruit, or entire trees. Three dimensional models, such as polygon mesh models may be derived from point clouds. 3D laser scanners are commercially available (e.g., from Tiger Supplies Inc., Irvington N.J.; Laser Design and GKS Services, Minneapolis, Minn.; Riegl USA, Orlando, Fla. and Faro USA, Lake Mary, Fla.). In some embodiments, waveform LiDAR (e.g., available from Riegl, Orlando, Fla.) is utilized, and in yet other embodiments discrete LiDAR is utilized.

According to some embodiments of the invention that utilize discrete LiDAR systems, when a sensor emits a laser pulse, the laser pulse will typically reflect off an object in the environment, and return to a light-detecting sensor. Several measurements may be taken on a single pulse returned to the light-detecting sensor, such as for example, the range to the object, the sensor time, the angle relative to the sensor, and the intensity of the returned pulse. The sensor time corresponds to the precise time the measurement was taken and is used to georegister measurements taken by the sensor. Specifically, the sensor time is the time a recorded echo is received at a receiver. The position of the sensor is also correlated to the sensor time, allowing the measurements to be related to the sensor position. In some embodiments, the sensor time may be determined based in part on attributes of the sensor. For example, a sensor may be configured to emit pulses at a predetermined frequency, such as for example, a certain number of pulses per second ("PPS"). This may be used to assist with the determination of the precise time that a measurement was taken.

In some embodiments, a second pulse is primed and emitted at a specific interval after the first pulse has been emitted. Discrete LiDAR systems may also record multiple returns from a single emitted pulse, indicating that the pulse reflected off multiple surfaces.

According to some embodiments of the invention that utilize waveform LiDAR systems, the returned laser pulse is separated into three dimensions: reflection; intensity; and pulse width. The extracted waveform is fitted to a smoothed pulse waveform using a Gaussian technique, which provides a continuous measured signal. Whereas discrete LiDAR provides a sample of range data points, waveform LiDAR may provide information at each point along the surface of an entire object. Because waveform LiDAR produces a continuous signal, it is generally more accurate and provides more detailed measurements than discrete LiDAR. Specifically, the reflectance, intensity and pulse width of waveform LiDAR yields higher point density measurements, and captures the intricacies and details of foliage grown on trees.

Further, waveform LiDAR is capable of measuring calibrated reflectance of a returned laser pulse which enables the system to isolate physical attributes of a plant. The signal measured at the light-detecting sensor is converted to a digital signal, to produce an amplitude reading and obtain a measurement of the echo width defining the vertical distribution of a target's surface as well the surface roughness of the target in question. The amplitude reading from the recorded waveform may then be compared to the emitted waveform and normalized accordingly. The normalized amplitude reading may then be calibrated to yield reflectance. The reflectance value associated with a particular amplitude reading is determined by utilizing a lookup table that correlates range-dependent amplitude readings with reflectance. In some embodiments, the waveform LiDAR sensor performs on-board full waveform calculations in real-time. In a preferred embodiment of the invention, the 3D laser scanner is configured to operate at a frequency of 550,000 points per second, which yields an optimum density and coverage.

In some embodiments, high-speed, high-density (HD) video is used to capture images of fruits and tree or vine features. The quality of video captured is important for accurate analysis. In some embodiments, video that is uncompressed 1080p at a speed of 60 frames a second or faster is utilized. In some embodiments, a fisheye lenses of 160° or greater is utilized. In yet further embodiments, cameras capable of capturing video of even higher definition or resolution can be used, such as for example, Ultra High Definition or 4 k, which are capable of displaying at least 8 million active pixels. These cameras may also be used in conjunction with one another to provide depth information (e.g., stereo vision) or various panoramas that cannot easily be achieved with a single camera.

Infrared thermography (IRT), thermal imaging, and thermal video are examples of infrared imaging science. Thermal imaging cameras detect radiation in the infrared range of the electromagnetic spectrum (roughly 9,000-14,000 nanometers or 9-14 μm) and produce images of that radiation, called thermograms. Since infrared radiation is emitted by all objects above absolute zero according to the black body radiation law, thermography makes it possible to see one's environment with or without visible illumination. The amount of radiation emitted by an object increases with temperature; therefore, thermography allows one to see variations in temperature. This is particularly useful when dealing with plant species that have very dense leaf coverage since the temperature differential between the leaf and the fruit is significant. The measurable temperature difference between the leaves and the ambient air can also provide important information about the vigor of the plant. High speed HD video hardware is commercially available (e.g., from NAC Image Technology, Simi Valley, Calif.; Olympus, Tokyo, Japan; Panasonic). Thermal imaging equipment is commercially available (e.g., from FLIR Systems, Boston, Mass. and L-3 Communications, New York, N.Y.).

In some embodiments, the capturing of this data requires specialized equipment mounted to the transport vehicle. In some embodiments, the transport vehicle can be for example, a 4 wheel drive, flying vehicle, off road vehicle, or any other suitable ground-based vehicle. The transport vehicle may be, for example, a John Deere Gator™ Utility Vehicle. In some embodiments, the transport vehicle may be an airborne vehicle. The transport vehicle can be a manned or unmanned vehicle that drives on the ground or flies low to the ground to transport the mapping hardware and other equipment throughout the area to be surveyed. Unmanned transport vehicles can be self-driving or remotely controlled. In some embodiments, a single data collection unit is capable of scanning two acres or more (e.g., 5, 10, 12, 15 or more) per hour in terrestrial applications.

Figure 7A:
FIGS. 7a, 7b, and 7c show exemplary user interfaces for controlling a data acquisition component, a transport component, and sprayer according to some embodiments of the invention.
Figure 7B:
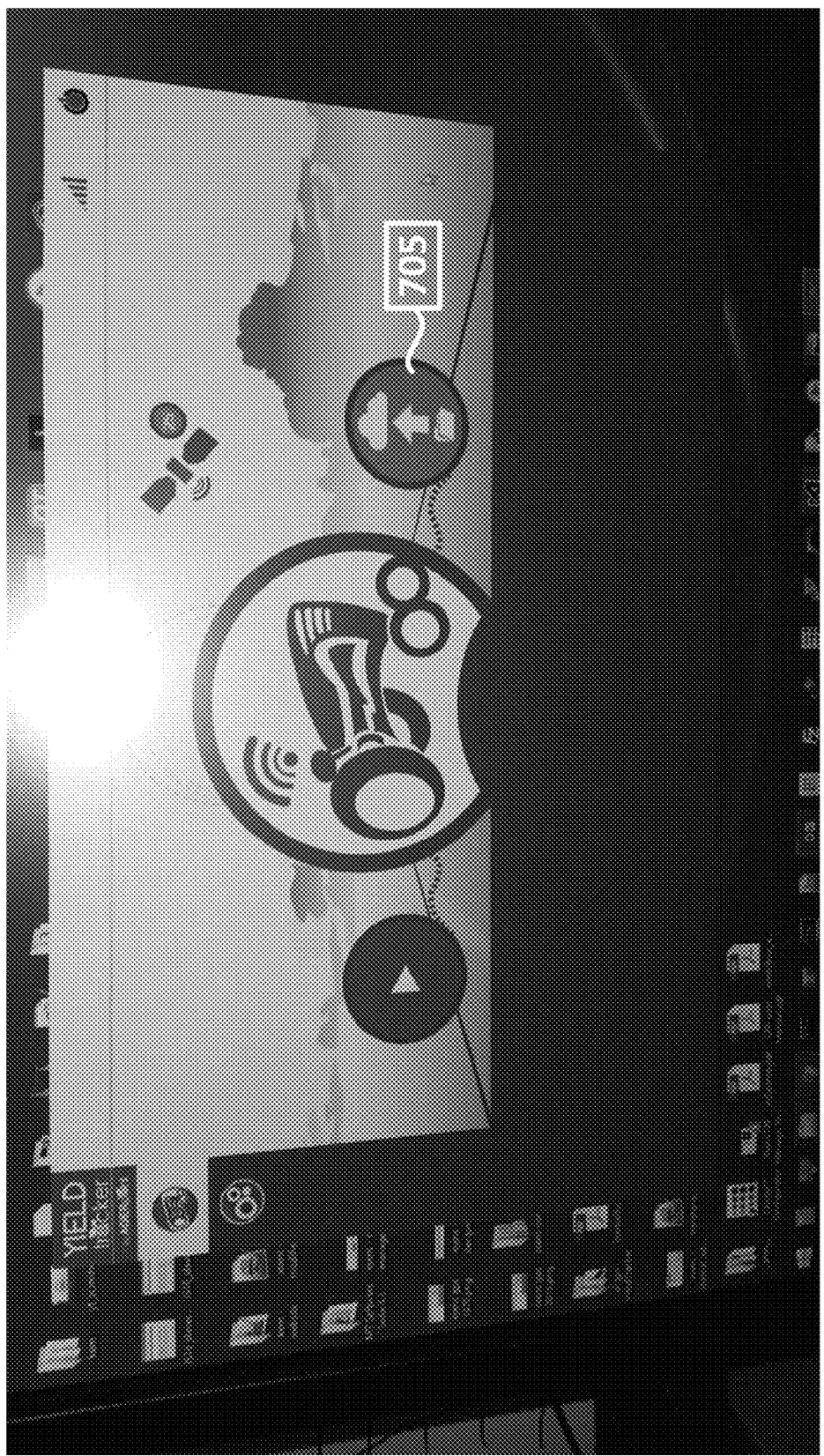
Figure 7C:
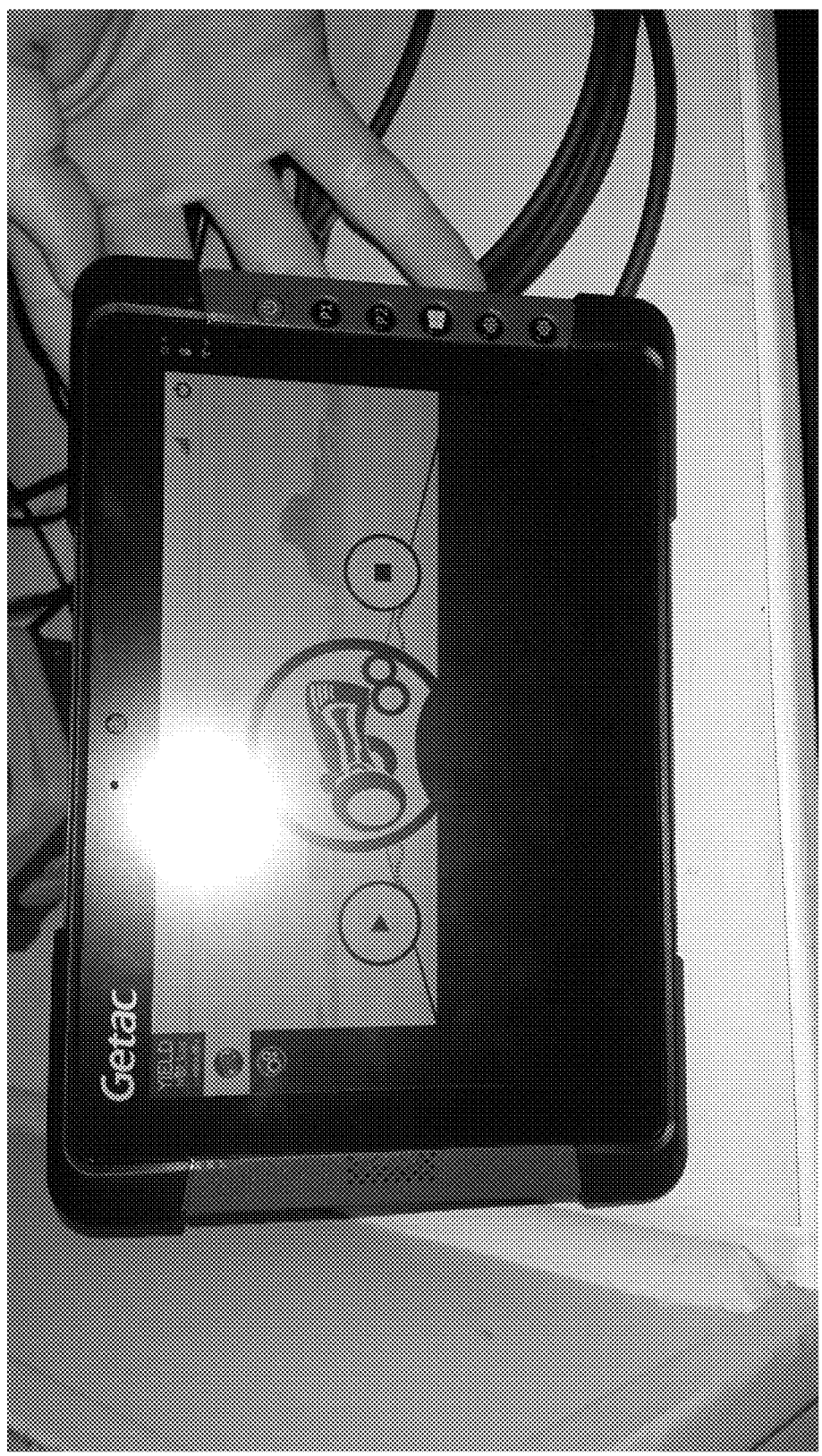

In some embodiments, the data acquisition component may include a user interface as shown in FIGS. 7*a*, 7*b*, and 7*c* for controlling a data acquisition component and transport component. According to the embodiments shown in FIGS. 7*a*, 7*b*, and 7*c*, the user interface may include icons and selectable buttons for controlling the collection of data and displaying the status of the data acquisition component, transport vehicle, software, and hardware. For example, as FIG. 7*a* shows, the user interface may include a start button 701 for beginning the collection of data, a stop button 702 for stopping the recording of data, an icon 703 for showing the speed of the transport vehicle, and one or more icons 704 that show the status of internet or wireless connectivity of the data acquisition component's wireless transceiver, and the signal strength of its GPS receivers. As shown in FIG. 7*b*, the user interface may further include an upload button 705 for transferring the collected data to a remote server. The icons shown in FIGS. 7*a* and 7*b* may be depicted in different forms at different locations of the user interface. As shown in FIG. 7*c*, the user interface may be provided on a mobile device, such as a tablet, PDA, or smart phone. In some embodiments, the user interface may be on a remote system, or a central dashboard computer.

In some embodiments, the present invention provides data analysis software and computer hardware configured to analyze data from the GPS, INS, scanners and video cameras described herein. In some embodiments, analysis systems include user interfaces and display systems. For example, the 3D scanner creates a point cloud which is a set of vertices in a three-dimensional coordinate system. These vertices are usually defined by X, Y, and Z coordinates, and are typically intended to be representative of the external surface of an object. When combined with positional data from the GPS and INS, the vertices may be mapped onto a geodetic coordinate system.

In some embodiments of the invention, the different datasets described above are synchronized with each other using timestamps that indicate when the data was captured. For example, each location recorded by the GPS may be associated with a timestamp of when the location was recorded. Similarly, each LiDAR measurement recorded by the 3D laser scanner may be associated with a timestamp. The GPS and LiDAR data may then be synchronized by matching the timestamps of the two datasets. In some embodiments, the sensors are integrated into a single sensor system and are coupled to a single clock which makes synchronization of the data possible without using timestamps.

In some embodiments of the invention, the INS and GPS systems are used to translate measurements taken by other sensors into real-world geodetic coordinates. As described in more detail below, measurements taken by a sensor (e.g., a 3D LiDAR scanner) may be initially recorded in a scanners own co-ordinate system ("SOCS"). The SOCS is a coordinate system that uses the sensor as the reference frame, and all measurements collected by the sensor are in relation to that sensor's reference frame. For example, when the 3D LiDAR scanner generates a point cloud, the coordinates of each vertex in the point cloud are based on the sensor's SOCS. In order to translate the measurements from the sensor's SOCS to real-world geodetic coordinates, the software component may use the INS positional data. Specifically, the software component may use the IMU coordinate reference frame to translate the SOCS coordinates to geodetic coordinates. For example, the software component may apply a rotational matrix and X-Y-Z translation to perform this translation into the IMU's reference frame. The rotational matrix may be a 3×3 rotational matrix. The software component may then use the time-stamps of the INS to correlate the SOCS coordinates of the sensor with real-world geodetic positions. In this way, the software component may translate the SOCS of the sensor measurements into the reference frame of the inertial navigation system. For example, using the known real-world coordinates of the LiDAR scanner as determined by the INS and GPS, the software component may then determine the location of any vertex in the LiDAR scanner's SOCS. The high levels of accuracy achieved by the INS and survey grade GPS systems enable the software component to translate positional information from a sensor's SOCS into real-world geodetic coordinates with a sub centimeter level resolution. Thus, the precise location of a vertex in a point cloud may be mapped into real-world geodetic coordinates.

In some aspects of the invention, the orientation measurements obtained by the IMU may be integrated into the analysis and mapping of point cloud data in three-dimensional space. The IMU may be used to determine the orientation of the sensor's reference frame, accounting for any angular rotation or positioning of the sensor with respect to the other components of the system. For example, if the 3D LiDAR scanner is positioned at an angle with respect to the ground, the 3D LiDAR scanner's SOCS will similarly be at such an angle. To account for the angular rotation of the data recorded in the SOCS, the software component may apply rotation matrices to the SOCS that rotates and maps the SOCS data into real-world geodetic coordinates. By combining orientation data with GPS positional data, the systems and methods may detect skewed data points from poor registration to a mapping frame. For example, orientation data may detect when a tree is leaning in a particular direction. With the integration of orientation data, the vertices of the point cloud may be calibrated to account for angles that may distort the 3D laser scanner data, resulting in a more accurate mapping of the vertices in three-dimensional space. In turn, the extraction of morphology attributes and phenotypes are more precise than an extraction based on LiDAR and GPS positional data alone.

In some embodiments, point clouds of trees and vines are collected to determine the height of the plant, the trunk diameter, and the leaf density, each of which correlates with health and productivity and each of which can be derived as part of an automated process called classification. The classified data is then loaded, another automated process, into the database for access by the end user.

In some embodiments, software analyzes image data on a per tree or per vine basis. In some embodiments, data collected for a particular tree or orchard is inserted into a relational database providing connectivity to other industry standard software products. In some embodiments, software performs one or more (e.g., all) of the following functions: a) assembly of point cloud; b) correlation of data to map coordinates; c) refining of video data; and d) geo-registration of all data that is collected, including for example, data from the survey grade GPS, the thermal imaging sensors, the radio, sound and magnetic wave sensors, the multispectral and hyperspectral sensors, the high-speed, high-density (HD) video camera, and point cloud data from the 3D laser scanner. In some embodiments, the following information is provided to an end user: tree trunk diameter, height of tree, volume of tree, leaf density of tree, color of leaves on tree, GPS location of tree, bar code data for tree, number of blossoms on tree, number of fruit on tree, and an annotated or un-annotated photograph of the tree (see e.g., FIG. 1).

In one aspect of the invention, the software component processes the data to automatically extract the morphological attributes of a tree. Models based on point cloud data may be used to extract morphological attributes, such as plant height or trunk diameter. As another example, the models may be used to perform segmentation and extraction of structural geometry. For example, the software component may search for boundaries of the three-dimensional point-cloud or other sensor data. In some embodiments, the boundaries are identified by analyzing a change between two data point values. Algorithms that determine similarity and rate of change from data point to data point using features such as color, pattern, or distance may be used to classify points as belonging to specific objects. A change of more than a threshold amount may represent an edge condition, which signifies the end of an object, or the beginning of another. These edges mark boundaries that can be used to classify each of the objects in an image or point cloud. After finding a boundary, the software component may identify a canopy, and then a trunk. The software component may identify a canopy by looking for a boundary or edge condition within a specific height range. To automatically extract a trunk, the post-processing server may attempt to identify a series of arcs in the three-dimensional point-cloud. The software component may then attempt to fit the three-dimensional point-cloud into a cylindrical shape. The portion of the point cloud having a best cylindrical fit may be identified as the plant trunk. The software component may then extrapolate plant trunk height.

In some embodiments of the invention, the morphological analysis segments and classifies features further, identifying branching structure, trunk segmentation, biomass estimation, tree stand structure, forest canopy height, extent, fruit clustering, and similar dimensional and structural plant features. As described in more detail below, these attributes may be used to determine the health and yield potential of individual trees and complete horticultural systems. These attributes may also be used to determine genome, vitality, risk of damage from wind, access to sunlight, and whether a plant has sufficient resources for photosynthesis.

In some embodiments, the sensor data may be analyzed to classify and identify various objects on a plant, such as fruits or blossoms. For example, variations in color or distances from sensor data may indicate the presence of a certain material or object (e.g., an orange) in an image or point cloud of a citrus tree. In some instances, the variations in color or distance may be caused by an overcast shadow or change in sensor position. For example, an image of a citrus tree may include a shadow from fruit or branches from nearby citrus trees. When analyzing the image, the software component may incorrectly detect the shadow edges and identify the shadow as a fruit. To account for such false positives, the software component may use the point cloud data to confirm the presence of fruit. Specifically, if there is fruit, then the point cloud will be in the shape of the fruit and indicate the presence of volume. However, if there is no fruit, the point cloud will be relatively flat, suggesting that the detected edge is merely a shadow.

In some embodiments, the variations are identified by analyzing a change between two pixel values. Algorithms that determine similarity and rate of change from pixel to pixel using features such as color, pattern, or distance may be used to classify points as belonging to specific objects. For example, a DD scan with noise may be used. As another example, a Canny edge detection algorithm may be used. In yet further embodiments, the edge detection algorithms may utilize a Roberts edge enhancement operator or Sobel edge enhancement operator. A change of more than a threshold amount may represent an edge condition, which signifies the end of an object, or the beginning of another. These edges mark boundaries that can be used to classify each of the objects in an image or point cloud.

In another aspect of the invention, the software component processes the data to extract the phenotypes of the tree. A plant's phenotype is the physical expression of a plant's genetic heritage relative to its development in its environment. A plant's phenotype may be, for example, the physical expression of the plant's genotype in combination with other information germane to its health and productivity. The information germane to the plant's health and productivity may be, for example, environmental stressors. A plant's phenotype is unique for each tree. Thus, a citrus tree inflicted with a disease or suffering a drought will have a different phenotype than a healthy citrus tree having the same exact genotype.

The physical expression of a plant's phenotype may be detected in part by its chemical composition. This, in turn, may be captured and measured with multi-spectral or hyperspectral sensors. For example, a citrus tree inflicted with a disease or suffering a drought may have a spectral signature that is unique and distinct from a healthy citrus tree having the same exact genotype. The information germane to health and productivity may be recorded for each tree. For example, environment stressors such as temperature, weather, and similar microclimate conditions may be recorded for each tree. Such environment stressors may be measured by coupling atmospheric sensors for measuring atmospheric conditions to the data acquisition component. In this way, an agronomist may differentiate between plants that are unhealthy or unproductive due to systemic causes or causes that are genetic/unique to the plant. This in turn allows growers to identify problems that may impact an entire orchard.

The software component may create a library of plant phenotypes that span across a wide array of plant cultivars and varieties which have experienced varying levels of health and productivity. The library may then associate this information with the attributes that define the phenotype's physical expression, such as for example, a set of hyperspectral or multispectral signatures, and a set of morphological attributes. Thus, when a grower wishes to retrieve information about a plant, the grower may for example access the plant's genotype, a set of hyperspectral or multispectral signatures, and health and productivity conditions. The health and productivity conditions may include a history of the plant's environmental conditions, such as for example, a history of the plant's temperature, weather, and microclimate conditions.

In one aspect of the invention, a grower may use the library to analyze or compare phenotypes of different plants or groups of plants at different levels of granularity. For example, an agronomist may analyze the phenotype of a single tree and compare it to the aggregated phenotypes of the entire orchard. In this way, a grower may better identify and understand stressors that are impacting an orchard as a whole, and distinguish them from stressors that are impacting a single tree.

In some embodiments, the software component may rely on machine learning algorithms (e.g., deep convolutional neural networks) to perform some or all of the analyses described above. In these or similar embodiments, the software is capable of learning from past experience. This enables the software to become more accurate over time by relying on a growing amount of data it has observed. These embodiments remove the need for parameters in algorithms that must be defined for accurate analysis and enable all or any combination of the data to be used together.

In some embodiments, the present invention provides methods of analyzing fruit tree quality and growth, including but not limited to, counting blossoms or fruit on the tree or vine (green or ripe), geo-locating plant or trees, determining age and health of tree or vine based on trunk diameter, leaf density, leaf color and overall volume. These methods find use in a variety of research and commercial applications in the agricultural, finance, banking, commodities, property appraisal, and insurance industry.

In some embodiments, crop data is utilized to allow a user to predict crop harvest by counting hanging fruit and measuring trunk diameter, leaf density, leaf color, environmental conditions, weather, previous harvests, age, variety, and overall volume. This is accomplished by utilizing a process that collects data in three formats: point cloud via 3D laser scanning; geo-location data via survey grade GPS; and photographic data via High speed HD video and/or thermal imaging.

In some embodiments, the systems and methods described herein find use in identifying subspecies of a particular species of tree or vine.

In one aspect of the invention, the point cloud data is fused with the other datasets, such as spectral data, to determine information about the tree such as its health, ripening period, vitality, or age. For example, the software component may use the spectral data to calculate various vegetation indices across different spectral bands that provide insight into the plant's health. Exemplary vegetation indices are set forth in Table 1 below.

TABLE 1

| Vegetation Index | Legend Range |
| --- | --- |
| Normalized Difference Vegetation Index ("NDVI") | Poor = <0.2<br>Moderate = >0.2 to 0.2.9<br>Good = 0.3.0 to 0.38<br>Very Good = 0.39 to 1 |
| Leaf Area Index ("LAI") | Poor = <0.5<br>Moderate = >0.5 to 0.9<br>Good = 1-1.67<br>Very Good = >1.67 |
| Green Ratio Vegetation Index ("GRVI") | Poor = <2<br>Moderate = 2-3<br>Good = 3-5<br>Very Good = 5-8 |
| Green Atmospherically Resistant Index ("GARI") | Poor = <0.1<br>Moderate = 0.1-0.2<br>Good = 0.2-.39<br>Very Good = 0.4-1 |
| Soil Adjusted Vegetation Index ("OSAVI") | Poor = <0.1<br>Moderate = 0.1-0.15<br>Good = 0.15-0.25<br>Very Good = 0.25> |

The NDVI may be used as a measure of general vegetation health. As shown in the associated Legend Range, a higher NDVI indicates a healthier plant. The LAI may be used as a predictor of crop growth and yield estimation. As shown in the associated Legend Range, a higher LAI indicates a higher crop growth and yield potential. The GRVI may be used as an indicator of a plant's photosynthesis. As shown in the associated Legend Range, a higher GRVI indicates a higher rate of synthesis. The GARI may be used to indicate a plant's chlorophyll concentration. As shown in the associated Legend Range, a higher GARI indicates a higher concentration of chlorophyll. The OSAVI is similar to NDVI, but suppresses the effects of soil pixels. The OSAVI is used in areas where vegetative cover is low (i.e., <40%) and the soil surface is exposed, causing the reflectance of light in the red and near-infrared spectra to skew vegetation index values. As shown in the associated Legend Range, a higher OSAVI indicates a better vegetation cover.

Figure 6A:
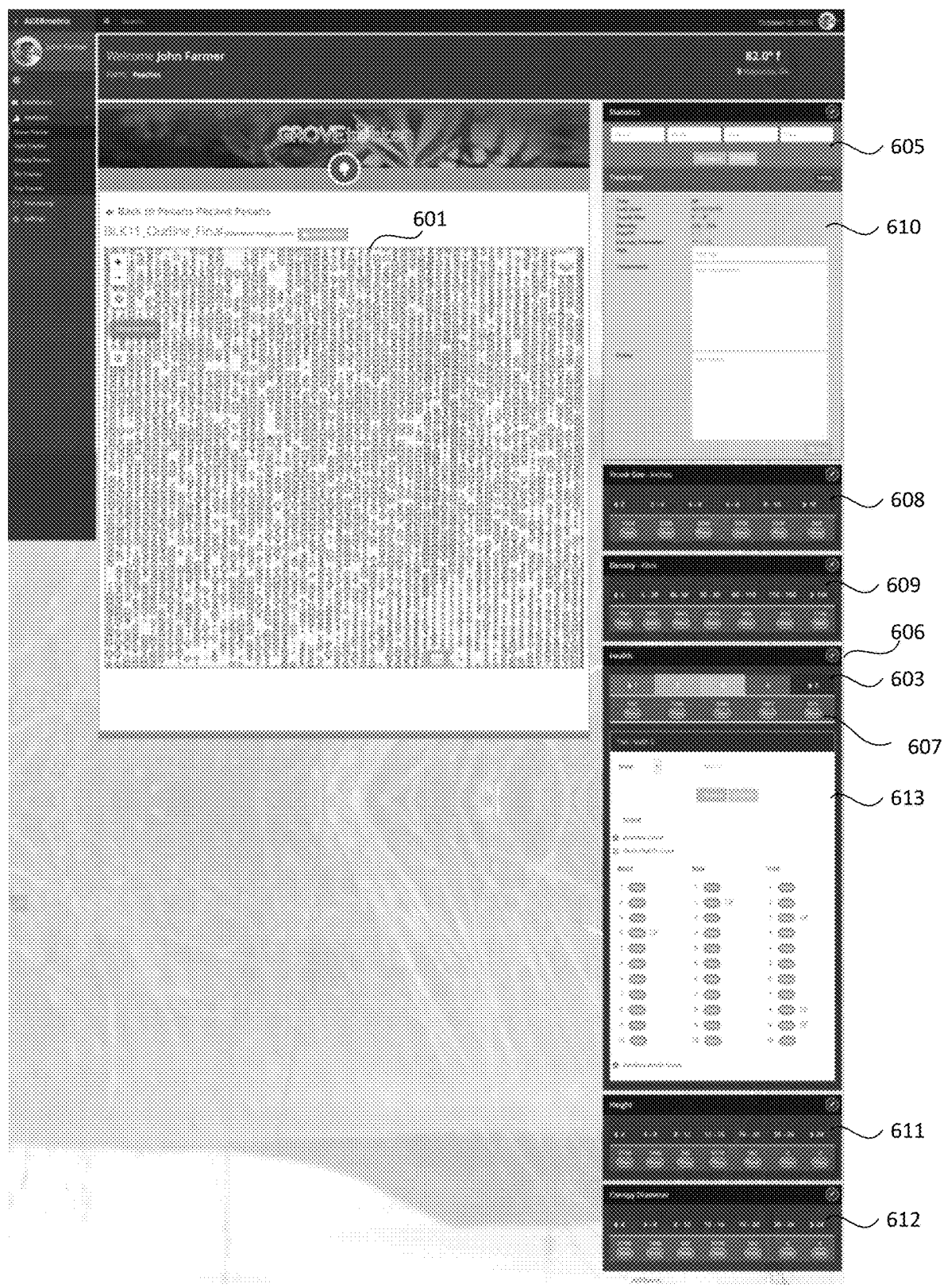

As shown in an exemplary embodiment as FIG. 6a, a tree's health may be displayed on a user interface and expressed numerically on a color-coded scale, with 1 indicating that the tree's health is poor and 5 indicating that the tree's health is above average. After determining each tree's health score, a map may be rendered showing each tree in a grove having a color that correlates to the tree's health.

The fusion of data additionally facilitates the sizing and counting of fruits or blossoms on a tree, thereby improving the prediction of a tree's yield. For example, the fusion of red, green, and blue (RGB) spectral band data with point cloud data enables users to precisely identify clusters of point cloud vertices that correspond to fruits or blossoms. The determination of fruit size, quality, or counting may be aided by using a Shanon index, Gini coefficient, or machine learning algorithms. The photogrammetric data, point cloud data, and spectral and thermal imagery are used to analyze factors such as plant color, geometry, and texture. Statistical and analytic functions may be used to differentiate blossoms and fruits from leaves and branches. Machine learning techniques may also be used to identify blossoms and fruits. For example, the vertices may be clustered using a density-based spatial clustering of applications with noise ("DBSCAN") algorithm. The DBSCAN algorithm relies on a density-based notion of clusters which is designed to discover clusters of arbitrary shape. Clusters are defined as a maximal set of density-connected points. The parameters of the DBSCAN algorithm may be configured to specify a desired size of a neighborhood and a desired density within the neighborhood. In other embodiments of the invention, the clusters may be identified using an octree K-means isodata clustering algorithm to identify clusters.

In some embodiments of the invention, clusters of data points may be identified by generating a training set based on one or more fruit or blossom attributes, and classifying a cluster based on the training set. For example, a training set may be generated using a grape vine having several grape clusters. Various attributes of the grape clusters may be measured to complete the training set, such as the grape clusters' range of reflectance values, the range of pulse shape deviation, other attributes related to full waveform data, and their spectral signatures. The software component may then use the clustering techniques described above to classify new grape clusters, but it may also utilize other machine learning algorithms like neural networks.

Figure 8A:
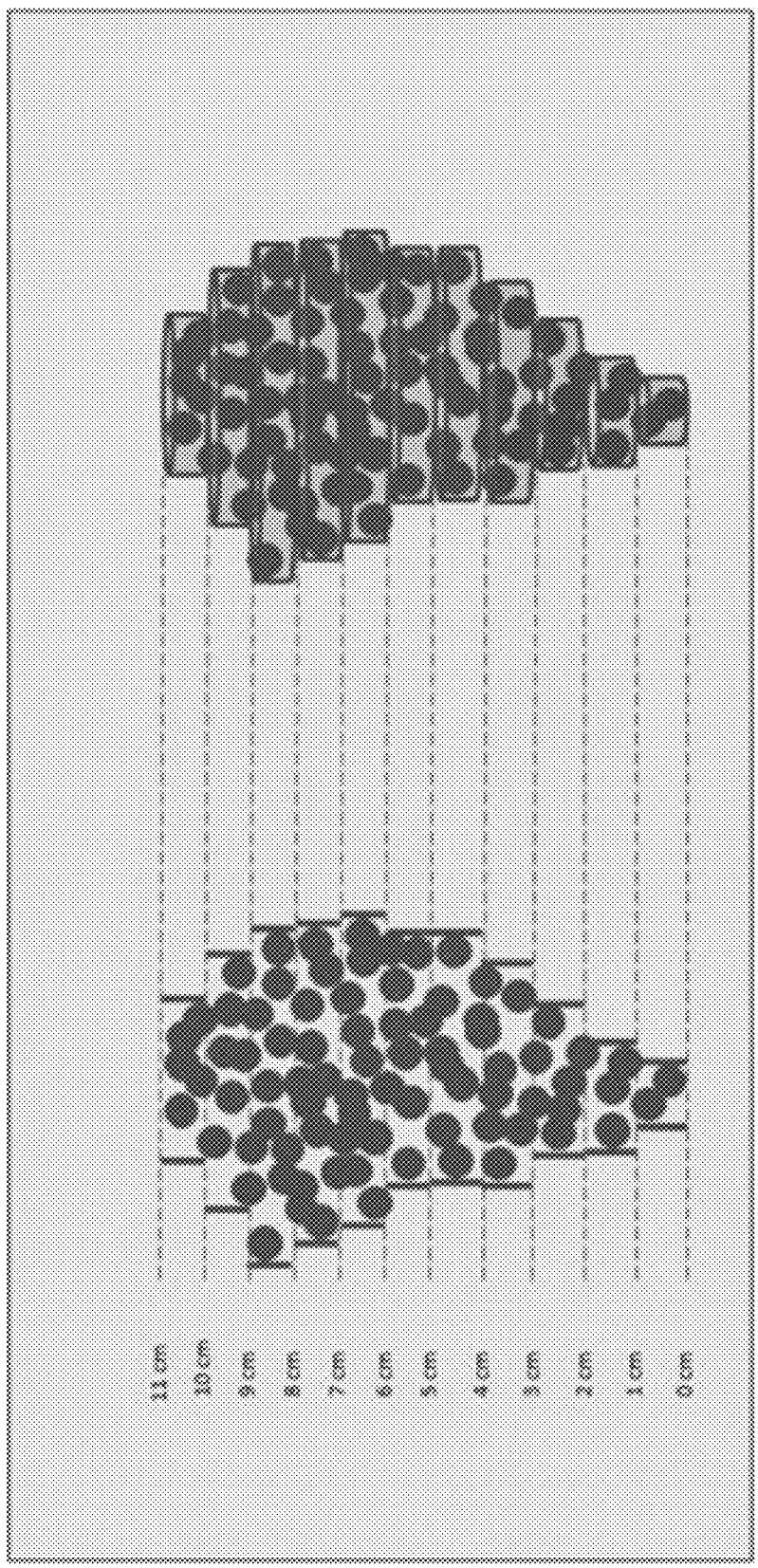
FIGS. 8a and 8b show examples of a data set being sized and counted based on clustering algorithms according to some embodiments of the invention.
Figure 8B:
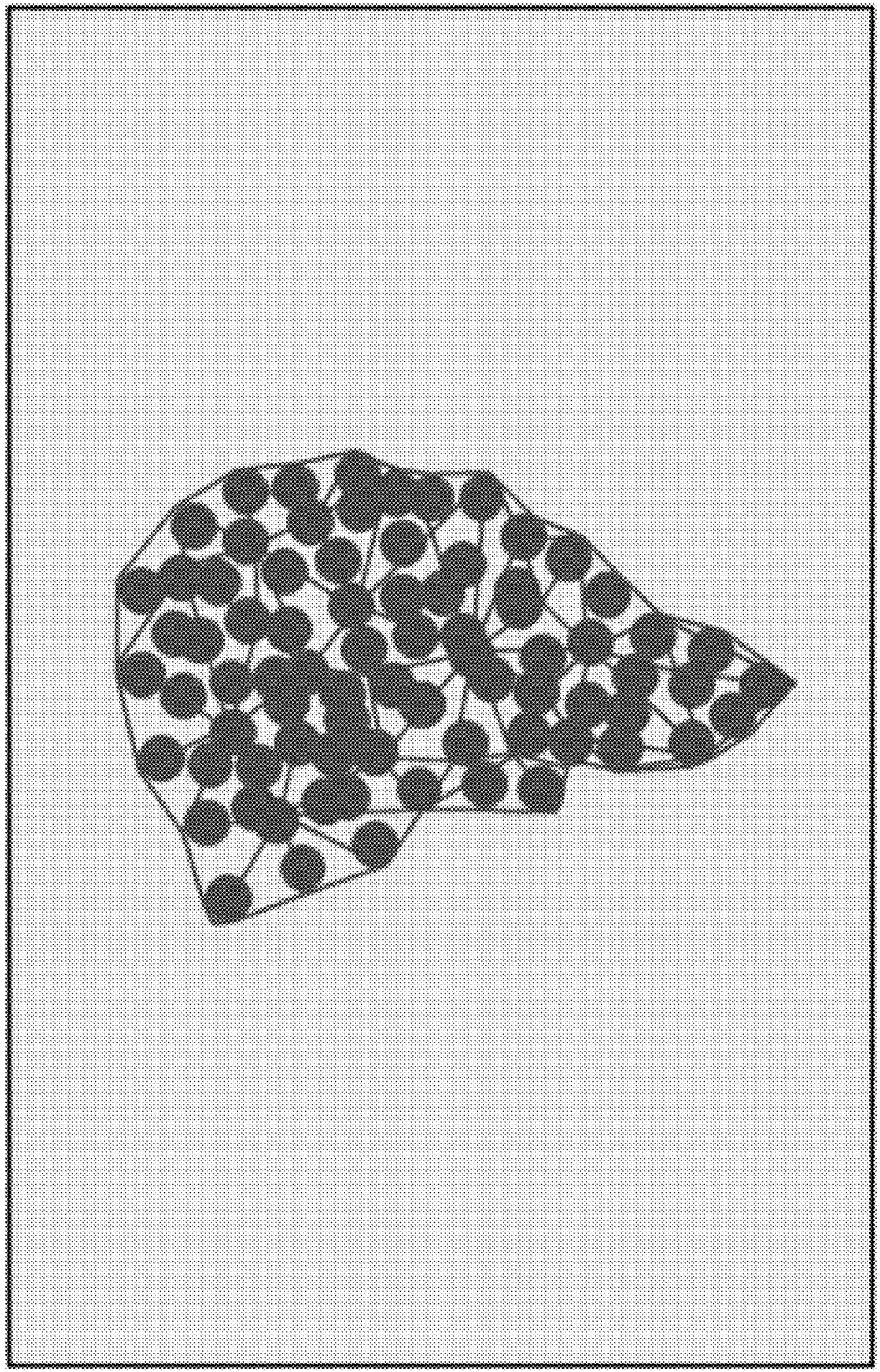

The software component may use the cluster information to determine the size and/or volume of fruit and blossoms on a plant. As shown on FIG. 8a or 8b, the volume may be determined using a vertical cylinder method or by generating a convex hull/mesh based on point cloud data. In some embodiments, clusters can be classified by determining a threshold number of point cloud vertices within a threshold area. For example, if there are more than 300 point cloud verticies within a 10 cm distance of each other, the area or volume encompassing these vertices may be identified as a cluster. An octree K-means/Isodata clustering or similar techniques can be used to locate these clusters. In some embodiments of the invention, the volume may be further based on ground truth data collected by a harvester. For example, if a harvester has measured the amount of volume or weight of fruit or crop generated by a specific plant, the software component may modify the volume estimation of a cluster given the known volume production of the plant.

In some embodiments, the systems and methods described herein find use in detecting disease (e.g., through the addition of multispectral and/or hyperspectral sensors). Hyperspectral imaging works by the development of a digital fingerprint. Unlike a conventional digital camera, which uses the three RGB bands, multispectral and hyperspectral imaging can use data from a greater range of the electromagnetic spectrum. Multispectral imaging may have on the order of one to ten bands where hyperspectral imaging may use tens to hundreds of bands. For example, there are approximately 250 sub-species of pecans in the US and the pecan tree has a particular signature in the electromagnetic spectrum and each of those sub-species have related but unique signature.

As described above, the software component may create a library of plants that have experienced a diverse array of health or productivity conditions. The library may associate these plants with their corresponding hyperspectral or multispectral signatures. The software component may then use this library as a classified data set for identifying correlations between various factors. For example, as described in more detail below, the library may be used to detect the presence of various conditions (e.g., diseases) in a plant given its hyperspectral or multispectral signature. That is, after the software component determines the hyperspectral or multispectral signature of a new or unknown plant, it may compare it against the library of hyperspectral or multispectral signatures. If the new plant's signature matches the signatures of diseased plants for example, then the software component may determine that the new plant has a specific type of disease.

The software component may compare the hyperspectral or multispectral signatures of the new or unknown plant by deriving spectral information divergence of the signatures. The spectral information divergence provides a spectral similarity measure between two pixel vectors X and Y. It quantifies the spectral discrepancy by making use of the relative entropy to account for the spectral information provided by each pixel. The smaller the value of the spectral information divergence, the smaller the differences between two spectral pixels. In a similar manner the morphological properties determined for a plant may also be used to determine relative plant health or cultivar and sub-cultivar.

In some embodiments of the invention, the hyperspectral sensors may include active sensors. Passive hyperspectral sensors typically measure spectral data based in part on reflected sunlight. Thus, hyperspectral data is typically gathered during the day time and when light conditions are at their peak. Active hyperspectral sensors, by contrast, typically provide an independent source of energy or illumination, and a sensor for detecting its reflected energy. In some embodiments, the hyperspectral sensor may include a sourced laser, operating between 900 nm and 1650 nm with 4 nm bands. Because active sensors are equipped with an independent source of light, active hyperspectral imaging may be performed at night or in areas that lack or are blocked from sunlight. Several advantages to performing hyperspectral imaging of trees and vines at night exist. For example, the quality or availability of spectral data retrieved from passive hyperspectral sensors may be impacted by shadows or weather conditions. Active hyperspectral sensors, by contrast, are not impacted by such variances, and allow growers to collect hyperspectral data at night or under a wide range of weather conditions. As another example, thermal imaging may be used to differentiate fruits from dense canopy and leaf coverings at certain times in the evening better than during the day. Specifically, because the water in the fruit causes its temperature to differ from the temperature in the leaves, the fruit are easier to discern from the foliage of the tree during the cooler temperatures of the night instead of the warmer temperatures of the day.

In some embodiments of the invention, the spectral data of the plants may be used to determine certain plant conditions such as its Nitrogen or chlorophyll content, the temperature of the leaves and hence the water status, or its sub-species. For example, the temperature difference between the leaves and the ambient air provides information about the level of water stress the plant is under.

As explained above, the health or productivity of a plant may be affected by certain stressors. Stressors may include internal factors that impact the functioning of the plant's systems, such as infection, infestation, injury, or poisoning. They can also include external factors that limit the plant's available resources, such as post-harvest growth, weed infestation, drought, and soil depletion. Some plants' reactions to stressors results in the diversion of specific chemicals to affected areas, which change the spectral signature of the plants. Plants may also respond with a physical change, such as wilt or leaf drop, causing differences in spectral signatures from the orientation of their leaves, the shape and edge conditions of their leaves, and their canopy density.

In the case of diseases such as "citrus greening", "blight" or "citrus canker," specific conditions are manifested in the leaf, trunk and/or fruit that change their spectral signature making them identifiable through machine vision techniques. Some diseases my also be observed by the changes they produce in the morphological characteristics of a plant. Citrus greening, for example, may lead to a less dense canopy compared to healthy trees. This reduction in canopy density may then be observed in the morphological features extracted from the data. Additional details are described, for example, in Lan et al., Applied Engineering in Agriculture Vol. 25(4): 607-615 and Kumar, Arun, et al. "Citrus greening disease detection using airborne multispectral and hyperspectral imaging." International Conference on Precision Agriculture. 2010. Each of these references are herein incorporated by reference in their entirety.

Blight is a wilt and decline disease of plants that when present in citrus trees ("Citrus Blight") can cause them to become unproductive, exhibit twig dieback, off-season flowering, and the production of smaller fruits. Symptoms typically associated with citrus blight include a mild wilt and grayish cast to the plant's foliage, high zinc content in trunk bark and wood, the presence of amorphous plugs in the xylem, the failure to absorb water injected into the trunk, and the presence of blight-associated proteins in roots and leaves. Blight is typically transmitted by root grafts; however, it is not typically transmitted by limb grafts or with budwood. Trees on all rootstocks are susceptible to Citrus Blight, but significant differences between stocks exist.

Citrus Blight is typically diagnosed on an individual tree in the field by testing water uptake into the trunk using a battery-powered drill and a plastic syringe without a needle. Trees affected by Citrus Blight take up no water regardless of the amount of pressure applied. For confirmation of Citrus Blight using the serological test, small numbers of samples of mature leaves may be collected and sent to a diagnostic lab.

Diseases can cause a wide variety of symptoms that affect the morphological and/or spectral signature of a plant. For example, citrus canker may affect plant production by causing defoliation, shoot die-back, and fruit drop. Symptoms include lesions and blemishes in the leaves, stems, and fruits of a citrus tree. Lesions may appear raised on the surface of the leaves, and in particular on the lower leaf surface. Pustules may also form on the surface, and eventually become corky and crater-like, with raised margins, sunken centers and surrounded by a yellow halo.

Certain types of citrus fruits are more susceptible to some diseases than others. For example, grapefruit, Mexican lime, and some early oranges are highly susceptible to canker. Navel, Pineapple, Hamlin oranges, lemons, and limes are moderately susceptible to canker, while mid-season oranges, Valencias, tangors, and tangerine hybrids are less susceptible. Tangerines are generally tolerant to Citrus Canker.

Citrus Canker outbreaks generally occur when new shoots are emerging or when fruits are in the early stages of development. Because the bacterium reside and reproduce in the lesions formed on the leaves, stems and fruit, the spread of Citrus Canker may be exacerbated by various weather conditions. For example, moisture or rain that collects on the lesions may cause bacteria to ooze out and spread to new growth or other trees. Weather conditions, such as frequent rainfall and warm weather, may also contribute to the prevalence of particular diseases. Wind-driven rain in particular is a significant dispersal agent of some bacterium. Wind speeds greater than 18 mph may cause the bacteria to penetrate through stomatal pores or wounds made by thorns, insects, and blowing sand. Heavy wind speeds may also cause the spread of the bacterium over greater distances. While long-distance spread of Citrus Canker may be caused by strong winds, the spread may occur more commonly with the movement of diseased plant material by growers and their employees. Specifically, workers and grove equipment can spread the bacteria within and among plantings, especially when trees are wet.

If major rainfall occurs during the critical time period that new shoots are emerging or when fruits are in the early stages of development, the likelihood of a Citrus Canker outbreak emerging grows significantly. Typically, leaf and stem infections occur within the first 6 weeks after initiation of growth, unless the plant has been infected by Asian leaf miners. Similarly, fruit are particularly vulnerable to infection when they are between 0.5-1.5 inch in diameter for grapefruit and 0.25-1.25 inch in diameter for oranges. After petal fall, fruit generally remain susceptible to Citrus Canker during the first 60 to 90 days for oranges or tangerines and 120 days for grapefruit.

Citrus Greening (also known as "Huanglongbing") is generally caused by the bacterium *Candidatus liberibacter asiaticus*. Like Blight and Citrus Canker, Citrus Greening affects tree productivity and causes tree decline. Root systems of infected trees are often poorly developed, and new root growth may be suppressed. Affected trees may show twig dieback, causing their productivity to decline, or stop altogether. The disease may impact the fruit produced by the tree, causing the fruit to be fewer in number, smaller, lopsided with a curved central core, discoloration. The disease may additionally cause fruit to drop prematurely from the afflicted tree. The affected fruit often contain aborted seeds and have a salty, bitter taste. When psyllids are abundant and conditions are favorable, the disease can spread, destroying existing groves and preventing the commercial production of oranges and other citrus cultivars.

Early symptoms associated with Citrus Greening include vein yellowing and an asymmetrical chlorosis (referred to as "blotchy mottle") on leaves, smaller-sized and upright leaves, and leaves that exhibit a variety of chlorotic patterns that often resemble mineral deficiencies such as those of zinc, iron, and manganese. Normally symptoms are severe on sweet orange, mandarins, and mandarin hybrids; and moderate on grapefruit, lemon, and sour orange. Lime, pummelo, and trifoliate oranges are generally more tolerant. Additionally, the bacterium may be diagnosed by a Polymerase Chain Reaction (PCR) from symptomatic tissues.

In one aspect of the invention, the spectral data may differentiate between trees with diseases such as Citrus Greening, trees in decline, trees that are deficient in nutrients, and trees that are healthy based on the measured reflectance of the tree across certain spectral bands. For example, a tree with Citrus Greening may be characterized by a unique combination of reflectance values ranging from 10% to 40% across the 1200 to 2000 nm wavelength band. A healthy tree, by contrast, has a uniquely distinct set of reflectance values across this band. After the reflectance values for a particular plant across this wavelength band are measured, the software component determines whether the reflectance values are associated with a healthy tree or a tree infected with Citrus Greening.

In some embodiments of the invention, the use of spectral imaging allows growers to determine the difference between a leaf exhibiting a deficiency in a nutrient, such as for example, zinc, and a leaf that is healthy or diseased.

In some embodiments, the software component may be configured to perform a Brix analysis, allowing the growers to evaluate the sugar content of fruit throughout its development. Brix may be measured in degrees (° Bx) which corresponds to a hydrometer scale that determines the amount of sugar in a solution at a given temperature. The measure is relative to the concentration of one gram of sucrose dissolved in 100 grams of water (1° Bx). The ° Bx may be associated with the ripeness or quality of a fruit. For example, harvest-fresh pineapple has a Brix measurement of approximately 13° Brix. Natural degreening of pineapple may occur when pineapples are transported. This degreening process is not visible from the outside, however, may be detected by changes to its Brix measurement. Typical measurement values for a harvest-fresh pineapple on delivery are 14.2 to 14.7° Brix. If the measurement value is clearly below this range, the fruit is poor quality. High Brix values indicate a sweeter taste and that the fruit or vegetable will keep for longer.

By fusing LiDAR with other data sets, such as multi- or hyperspectral data, a grower is enabled to track disease vectors and determine how a condition is spreading across their property or throughout a specific region. A vector may be an agent (e.g., person, animal, or microorganism) that carries and transmits a pathogen into another organism. By mapping vectors and comparing them from time period to time period, it is possible to determine how a condition is spreading through an orchard, and postulate ways to minimize further transmission. The time periods for comparison may be for example, at the beginning or end of a growing season. In some embodiments, a grower may map the vectors at more frequent intervals, such as, for example, a monthly, weekly, or daily basis. The direction of travel of the vector may be identified using statistical methods and/or spatial models to analyze and predict the continued path of the vector. For example, maps of plants affected by a particular disease, such as for example, Citrus Blight, may be generated as a function of time. The maps may then be viewed together to show how the condition has spread over time across particular regions of a grower's orchard or plot.

In one aspect of the invention, a grower may be able to detect and track the presence of arthropod pests, such as aphids or spider mites. Pests may be detected and tracked by fusing LiDAR data with spectral data and thermal data where pests may be directly detected by their body or structures created by the pest or indirectly by observing physiological changes in a plant resulting from the pest. The degree of infestation, the rate of growth and potential direction of spread may be predicted based on spatial associations of plant morphologies, sub-species, terrain, or environmental conditions.

In one aspect of the invention, a history of each type of data (e.g., multi- or hyperspectral data) is associated with each plant, allowing growers to perform temporal analyses on each plant. Other attributes and data that may be temporally recorded for each plant may include the plant's date of planting, its variety, its root stock, its grafting record, its nutritional treatment, its health treatments, its yield, its surrounding soil conditions, its surrounding temperature, weather, and microclimate conditions, and topographical information. In some embodiments, a grower may define a custom data field that may be temporally monitored for each asset. The custom data field may include data entered manually in the form of alphanumeric, photographic or other data types, as well as calculated fields such as indices or predictions. The data fields may also be automatically maintained. For example, if the data field corresponds to data collected by a sensor, the data field may be automatically populated by data collected via a sensor. Some data fields may be populated from third party sources, such as for example, weather or soil readings. Other data fields may be manually entered on an ad hoc basis, and may be appropriate for monitoring activities such as remedial pruning or weed removal. As described in more detail below in reference to FIGS. 6a, 6b, and 6c, a history of grafting records for one or more plants may be viewed on a user interface that displays an interactive map of the plants in the grower's orchard.

In another aspect of the invention, a grower may monitor which plants its employees are handling. In this way, if a grower has identified a plant or area of plants as infected with a disease, the grower can limit or prevent an employee from coming into contact with another plant or area, to prevent the spread of disease.

In yet another aspect of the invention, a grower may track storm and dominant wind profiles in a plant's history. A "dominant wind profile" is a history of wind speeds and direction in an area surrounding a plant or orchard. This information be used to help predict and track the spread of diseases. In some embodiments, the storm and weather profiles may be used to predict and track the spread of diseases. For example, because rainfall and winds exacerbate the spread of Citrus Canker, past records or patterns of rainfall or wind gusts may be used to determine or predict whether Citrus Canker in one plant may have been dispersed to another plant or area.

In some embodiments of the invention, the data is used to extract health information below the level of the individual plant. In such embodiments, the health of individual branches or sections of the plant may be determined. For diseases that spread from one part of the organism to the others, this information may allow diseased portions of a plant to be removed before they impact the health of the rest of the plant.

As described above in reference to plant phenotypes, a library may be created that catalogues an assortment of plant cultivars and varieties having experienced varying levels of health and productivity, along with their associated physical attributes such as spectral signatures or plant morphology. In some embodiments of the invention, a grower may identify an unknown plant cultivar or variety using the information stored in the library. For example, a grower may compare the spectral signatures of the unknown plant to the spectral signatures stored in the library. Specifically, the plant's measured spectral data may be compared to the spectral data of each plant at various wavelengths in the library of cultivars and varieties to find a match. Any other information known about the foreign plant may also be used to further associate the unknown plant with a cultivar or variety. For example, environmental conditions, morphological attributes, or information about whether the plant is diseased may be used to confirm an association with a cultivar or variety. In this way, variety and cultivar information for each plant on a grower's property may be provided on a plant-by-plant basis.

In one aspect of the invention, the crop yield for a grove may be predicted based on the counting of fruits and blossoms as described above, as well as taxonometric information. Taxonometric information helps differentiate plants of certain subspecies from the overall species, and helps distinguish one plant variety from another. Taxonometric information includes any traits for categorizing the members of the dataset. For example, if the plant or fruit's condition is determined to be unhealthy or infected as described above, it will not be included in the predicted crop yield. Similarly, if the environmental conditions of the plant are characterized by drought or extreme temperatures, the predicted yield may be lowered according to the severity of the drought/temperatures. In some embodiments, predicted yield is calculated for each specific tree. As described in more detail below, the yield for each tree may then be aggregated at various different levels of granularity, such as by row, column, block, grove, geographic region, or market.

In some embodiments of the invention, the overall yield may be predicted based on the attributes of multiple plants, such as the leaf area index or canopy biomass. These are indicators of a plant's (or stand of plant's) ability to collect sunlight, and, by extension, produce sugars. Attributes such as branching patterns may be used to indicate variety or injury, which may affect yield.

In some embodiments, identification of subspecies or disease is performed simultaneously with the other data that is being collected (LiDAR, photos, etc.) and geo-registered via GPS along with the other data.

In some embodiments, the data collected using the systems and methods described herein finds use in guiding sprayers through real-time mapping or premapping (e.g., commercial sprayers). Spraying represents a very large part of the budget of a grower and using the right kind of spray (herbicide, pesticide, and/or nutrient), in the proper amount, at the right time can have a dramatic impact on the farmers profitability. In some embodiments, data is collected using the systems and methods described herein (e.g., trunk centroid, tree height, canopy density, canopy diameter, species of tree, longitude and latitude) are used to control the sprayers. This data (e.g., in csv format) tells the sprayer as it travels through the grove from precalculated data, on a per tree bases, when to spray, how long to spray, and what chemicals to spray.

In some embodiments, a prescription file is attached to a GIS shapefile using the GPS, point cloud data and classification data described above. The prescription file further includes spraying instructions that specify the location and type of spray to be applied to each tree. In some embodiments, the prescription information may include the spatial data, point cloud data, and classified data described above, such as tree height, canopy diameter, or leaf density, as well as other information such as morphological attributes, spectral data, cultivar/variety, age and phenotype. For example, a prescription file may contain a three-dimensional shape of a tree, the precise geographic coordinates of the tree, an instruction as to what spray to apply to the tree, and which part of the tree to spray. In this way, the spray may be applied to a particular tree or space within or surrounding a tree based on the sprayer's precise geographic location. In one aspect of the invention, a grower may control the application of a spray to a particular tree based on the extracted morphological attributes, spectral data, cultivar/variety, age and phenotype of the tree. For example, the grower may configure the prescription file to apply a first type of spray to a tree that is identified as a 80 year-old Oconee pecan tree, whereas the same prescription file may be configured to apply a second and distinct type of spray to a 45 year-old Summer pecan tree in the same row.

Some embodiments of the invention use the data to provide valuations of plants. The morphological and health properties determined for the plants provide helpful information when assessing the value of a piece of property and the plants on that property. This information can be useful to individuals looking to buy or sell property containing plants or for insurance companies looking to insure plants. Similarly some embodiments of the invention may be used to measure the status of plants after damage (e.g., after severe weather events). In such embodiments, the amount of damage can be quantified based on changes in the plant morphology and health. In one example, the amount of a tree canopy remaining after a catastrophic weather event can be measured along with the angle between the trunk and the ground. This information can be used to assess about how much value was lost after damage occurs and could be useful to entities like (but not limited to) insurance companies.

In some embodiments, the present invention provides computer implemented systems and methods for performing fruit tree analysis and displaying the results to a user. In some embodiments, computer implemented systems and methods generate a report of the results of the analysis methods that provide information (e.g., fruit yield, tree quality, harvest date predictions, sprayer coordinates) to a user. In some embodiments, the report is provided over the Internet (e.g., on a smart phone, tablet or other wireless communication device) or on a computer monitor.

Figure 9:
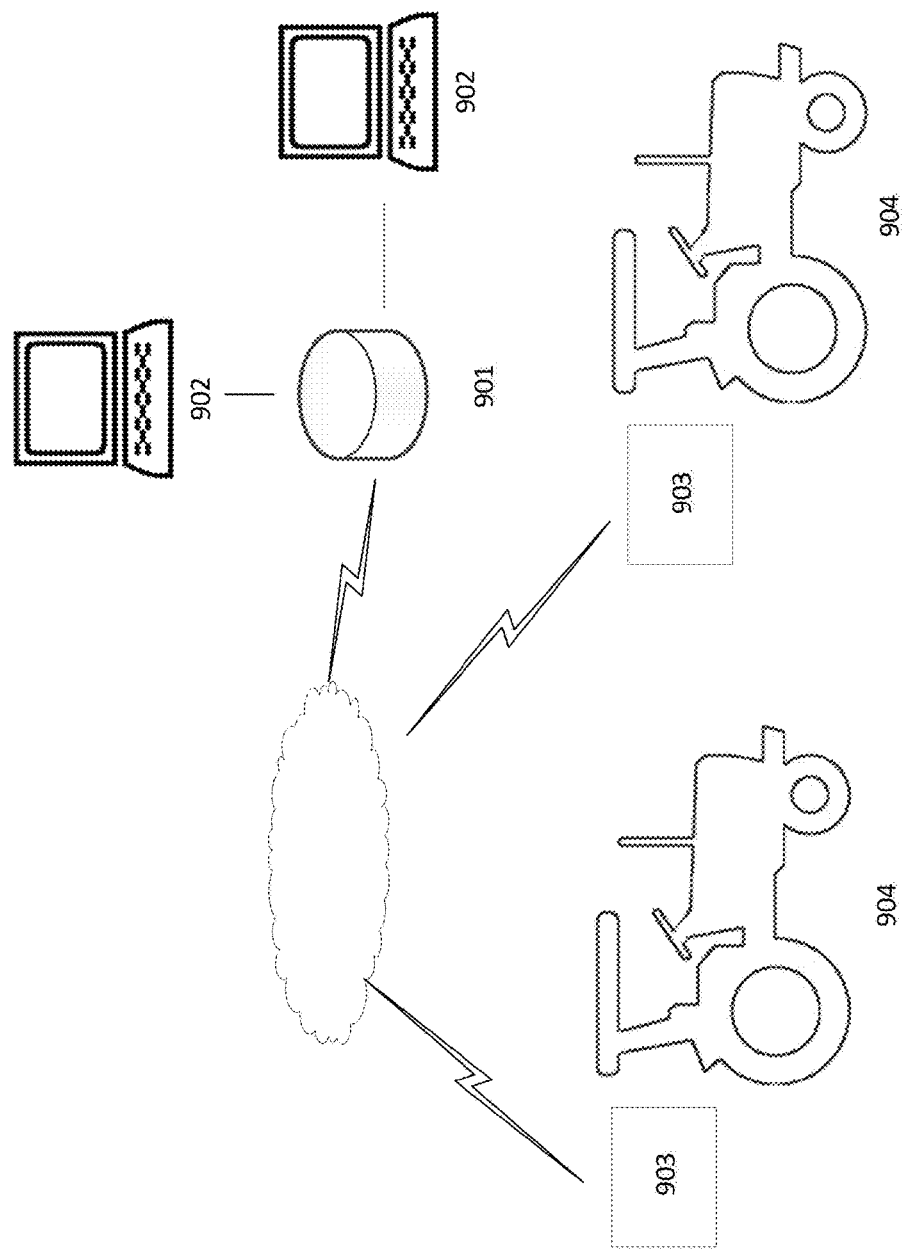
FIG. 9 shows a system comprising one or more transport vehicles and asset management dashboards according to some embodiments of the invention.

In some embodiments, the systems and methods of the present invention are provided as an application service provider (ASP) (e.g., can be accessed by users within a web-based platform via a web browser across the Internet; is bundled into a network-type appliance and run within an institution or an intranet; or is provided as a software package and used as a stand-alone system on a single computer). For example, as shown in FIG. 9, some embodiments of the invention may include a post-processing server 901 that performs the processing of data received from one or more software components or data acquisition components 903 mounted on one or more transport vehicles 904.

Figure 6B:
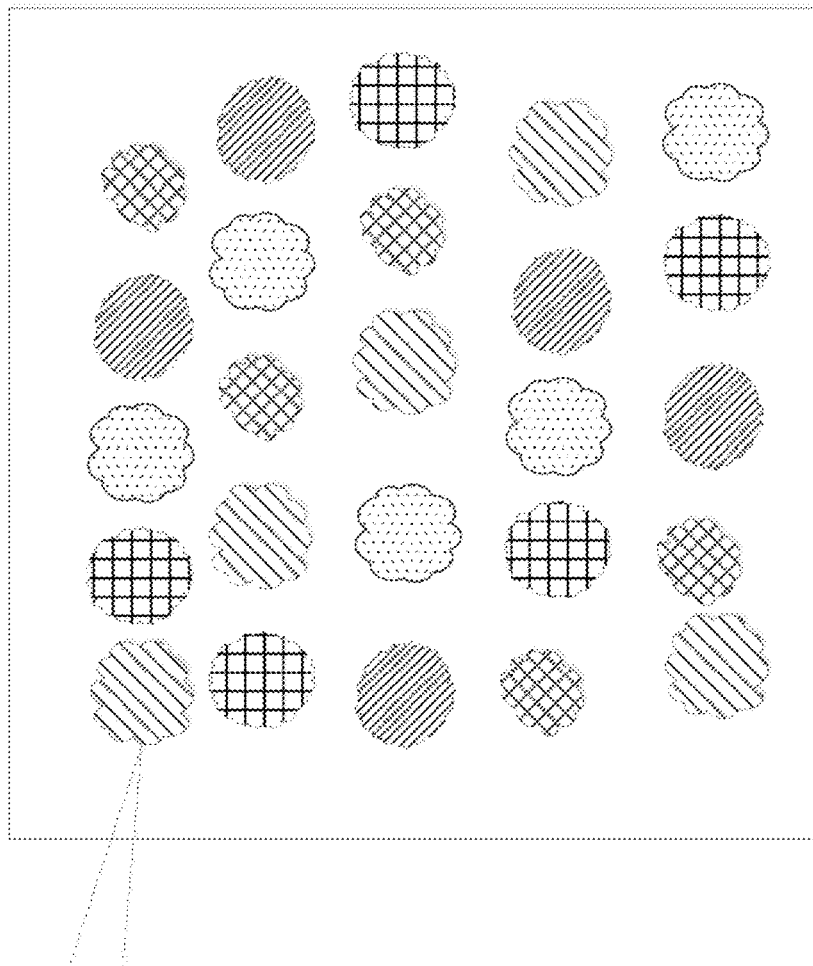

In some embodiments of the invention, the systems and methods include an asset management dashboard for accessing, viewing, analyzing and controlling the collected and analyzed data described above. Some embodiments of the asset management dashboard may be provided over the internet, in the form of a web page, as shown in FIG. 6a. The asset management dashboard may be used to render visualizations of the data collected by the data acquisition component or stored in a post-processing sever. For example, the visualization may include a map of the three-dimensional point clouds or a two-dimensional bird's-eye view of the orchard 601, or both. As described above, the map may render plants at a sub centimeter resolution, as well as any data collected from other sensors, such as the 3D LiDAR scanners, spectral sensors, video sensors, or thermal sensors, and any calculations or analyses associated with the plant, such as calculations or analyses related to the plant's morphology or phenotype 602. For example, as shown in FIGS. 6a and 6b, each plant rendered on the map may visually indicate the number of fruit or blossoms counted on that plant 602. In this way, the map may then be used to analyze the productivity of plants within the orchard or across a whole growing operation.

The asset management dashboard may further render a map of yield estimates at a sub centimeter resolution. As described above, yield may be estimated for a plant based on the three-dimensional point cloud data or other data collected by the various sensors of the data acquisition component, or any combination thereof. These estimates may then be displayed on a map with the other calculations described above.

In one aspect of the invention, the asset management dashboard may be used to view the health status for each plant in its property. For example, as shown in FIG. 6a, a tree's health may be expressed numerically on a color-coded scale 603, with 1 indicating that the tree's health is poor and with 5 indicating that the tree's health is above average. After determining each tree's health score, a map may be rendered showing each tree in a grove having a color that correlates to the tree's health. FIG. 6a illustrates a two-dimensional bird's eye view of the visualizations, however, in other embodiments of the invention, the color-coded scales may be overlaid onto the three-dimensional point cloud data for a three-dimensional visualization. For example, an interactive map showing several trees colored as red indicates that the trees in the grove are unhealthy. The scale thus provides a way for users to quickly recognize trees that require attention without detailed analysis.

In other embodiments of the invention, as shown in FIG. 6b, each plant may be associated with one or more layers sensor of data and detailed calculations and/or analyses 602. The additional layers of sensor data may be for example, photographic, video, or spectral sensor data. Each of the one or more layers of sensor data may comprise a plurality of data points that are geo-registered with the geodetic positions in the same manner as described above. Each data point in an additional layer of sensor data may be associated with one or more vertices of the three-dimensional point cloud. The asset management dashboard may then overlay the additional layers of sensor data on the three-dimensional point cloud. As shown in FIG. 6b, a user may select a particular plant, triggering the asset management dashboard to display the data or subsets of data that have been calculated and associated with the plant. The data may include morphological attributes, such as its trunk diameter or area, as well as geodetic positional data such as the latitude and longitude of the plant's centroid.

The asset management dashboard may also be configured to display a single layer of sensor data and detailed calculations and/or analyses. For example, as shown in FIG. 6c, a single layer may be the NDVI that is generated based on spectral data collected by the hyper-spectral or multi-spectral sensors described above. The NDVI data may then be overlaid on the same visualization of the plants shown in FIGS. 6a and 6b, allowing agronomists to easily analyze correlations between yield and spectral data for each plant. A legend 604 may be used to indicate the NDVI associated with each tree.

As another example, red, green, and blue (RGB) spectral band data obtained from a video sensor such as the video camera, may be overlaid with three-dimensional point cloud data to precisely identify clusters of point cloud vertices that correspond to fruits or blossoms. In this way, the fusion of data additionally facilitates the sizing and counting of fruits or blossoms on a tree, thereby improving the prediction of a plant's yield. The photogrammetric data, three-dimensional point cloud data, and spectral and thermal imagery may also be used to analyze factors such as plant color, geometry, and texture. Statistical and analytic functions may be used to differentiate blossoms and fruits from leaves and branches as described above.

In one aspect of the invention, the dashboard may integrate the spatial information about a plot to allow users to generate precise counting and statistical reports about the number of trees or vines and their health. The dashboard may further include one or more filters 605-612 for filtering the plants visualized in the user interface or provided in the report. For example, the dashboard may include a search box 605 that allows a user to query the precise number of trees that are healthy in a particular block, column, row, or geographic region. The dashboard may further allow a user to use his or her mouse to select an area (e.g., a rectangular region) on the map, and determine the number of healthy trees inside the region. The dashboard may include a health filter 606 comprising the color-coded key 603 that correlates plant health score to color. Under each health score, the dashboard may show the number of trees or vines with that particular score, and a selectable button for viewing which trees have that particular score. For example, when the user selects the "View" button 607 shown under the Health Score labeled as "5" and colored as green, the map is re-rendered to only show the trees that have a health score of 5, which FIG. 6*a* indicates is a total of 824 trees. The dashboard may also allow a user to submit a query to determine the health status for a particular tree by clicking on a tree in the rendered map, or submitting the tree's block, column, and row number.

In some embodiments, the dashboard may integrate spatial information about a plot with the extracted morphological attributes, phenotypes, or classification data described above. For example, the dashboard may include a window that shows the number of trees according to their trunk size 608. As shown in exemplary FIG. 6*a*, a window labeled "Trunk Size" shows that there are 1524 trees with trunk sizes less than 2 inches wide. Under the total number of trees with this trunk size is a selectable "View" button that, when clicked, re-renders the map to only show the trees that have a trunk size of less than 2 inches. Similarly, the dashboard may include a window that categorizes trees according to their leaf density 609, and other morphological attributes, such as height 611, and canopy diameter 612.

In one aspect of the invention, the dashboard may allow users to filter trees according to different combinations of selected morphological, phenotype or health attributes. For example, the dashboard may allow the user to query trees having both a trunk size of less than two inches and a health score lower than 2. In some embodiments, the user's selected criteria may be combined as logical Boolean queries. For example, the query the dashboard may allow the user to query trees having a health score lower than 2; and either a trunk size less than two inches or a leaf density smaller than 5. For example, a grower could look at trunks <3", canopy <6', and health <3, to see trees that may have a health problem that is stunting their growth.

As shown in exemplary FIG. 6*a*, the dashboard may further include a window 610 that allows users to record information about each plant's age, treatment, or other notes that are specific to a plant. When a user selects a plant, the asset management dashboard may display a scrollable popup window or menu with a table of information about each plant's age, treatment, or other notes that are specific to the plant.

As described above, some embodiments of the invention allow the predicted yield to be calculated for each tree within a grower's property. Using the asset management dashboard, a grower may aggregate the predicted yield data to determine the yield of a crop at various levels of granularity. In one aspect of the invention, the dashboard may allow a user to seamlessly and instantly alternate between high-levels of granularity that provide information about an orchard as whole and discrete levels of granularity that provide information about an individual tree. For example, a user may aggregate the predicted yield for each tree in a row, column, block or grove 613. As another example, the user may select a particular region of the grove, by for example selecting an area on the map with his or her mouse, and querying the predicted yield for the aggregate of trees in the selected region. In the same interface, a user may then select information about an individual tree. In this way, a user may draw comparisons between plants at different levels of scale that were previously not possible. In other embodiments of the invention, the user may submit a query for predicted yield in conjunction with other selected criteria, such as for example, the predicted yield for a particular subspecies or cultivar/variety of fruit.

In some embodiments of the invention, the predicted yield may be used in conjunction with methods and systems for measuring the actual yield produced by a tree. For example, the predicted yield may be compared to the actual yield of a windrow using Leddar as described in U.S. application Ser. No. 15/209,689, entitled "SYSTEMS AND METHODS FOR DETERMINING CROP YIELDS WITH HIGH RESOLUTION GEO-REFERENCED SENSORS" to K. Thomas McPeek, herein incorporated by reference in its entirety filed on Jul. 13, 2016. As another example, the actual yield may be measured using load cell weight measurements. The actual yields measured at a particular location in the windrow may be assigned to specific plants or regions within a grower's holdings. In this way, a grower may compare and verify the predicted yields for each plant to actual harvest data, and further, to alert growers to underperforming assets.

In one aspect of the invention, data may be collected and aggregated across properties owned by different growers. The aggregated data may be maintained anonymously and then used to generate yield predictions for a market as a whole. Market wide predictions may then be distributed to growers, financial organizations, commodities traders, governmental departments, agricultural and environmental agencies, or other parties with an interest in food prices.

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

What is claimed is:

1. A plant analysis system, comprising:
a) a data acquisition component configured to:
measure properties of a plant utilizing waveform light detection and ranging (LiDAR) to assemble point cloud data, wherein said point cloud data comprises a plurality of three dimensional vertices each of which represents an external surface associated with said plant;
collect photographic data of said plant;
collect spectral data for said plant; and
geo-register the point cloud data and photographic data; wherein the plurality of said three dimensional vertices of said point cloud data is associated with global positioning satellite (GPS) data, said photographic data, and said spectral data;
b) a transport vehicle on which said data acquisition component is mounted and configured to assemble and geo-register said point cloud data, and collect said photographic data and said spectral data on said plant; and
c) a processor configured to:
determine a spectral signature of said plant based on said spectral data;

determine plant color based on said photographic data and associate said point cloud data with said plant color; and generate morphological data of said plant based on said point cloud data, said morphological data comprising one or more of plant stem diameter, plant height, plant volume, and plant leaf density.

2. The plant analysis system of claim 1, wherein:
the processor generates said morphological data by segmenting said point cloud data to identify boundaries of said plant; or
the processor classifies said morphological data to identify a plant feature, said plant feature comprising a branching structure, trunk, biomass, canopy, fruit, blossom, fruit cluster, or blossom cluster.

3. The plant analysis system of claim 1, wherein the processor utilizes said point cloud data and said plant color to discriminate a fruit, blossom, fruit cluster, or blossom cluster from a shadow based, at least in part, on analyzing a variation of said plant color and a geometric shape defined by the three dimensional vertices of said point cloud data.

4. The plant analysis system of claim 1, wherein said data acquisition component is further configured to measure atmospheric conditions, and wherein said processor determines a phenotype of the plant based on said spectral signature, said morphological data, and said atmospheric conditions.

5. The plant analysis system of claim 1, wherein said processor is further configured to determine a vegetation index of one or more plants based on said spectral data.

6. The plant analysis system of claim 1, wherein said processor is further configured to determine a number and a size of fruits or blossoms on the plant, wherein the number and size of fruits or blossoms on the plant is based one or more of said point cloud data or said plant color data.

7. The plant analysis system of claim 6, wherein:
said number and size of fruits or blossoms on the plant is determined by clustering said point cloud data and plant color data; and
a crop yield is estimated based, at least in part, on said number and size of fruits or blossoms on the plant.

8. The plant analysis system of claim 1, wherein said processor is further configured to compare the spectral signature of the plant with a second spectral signature from a library of plant records.

9. The plant analysis system of claim 8, wherein said processor is further configured to:
detect a presence of a plant disease based on said comparison of the spectral signature with the second spectral signature;
detect a presence of wilt or leaf drop caused by environmental stressors based on said comparison of the spectral signature with the second spectral signature; or
identify a pest, including a disease vector, and predict said pest's trajectory.

10. The plant analysis system of claim 1, wherein a library of plant records is further configured to store historical data associated with the plant, said historical data comprising one or more of date of planting, root stock, grating record, nutritional treatment, health treatment, yield, surrounding soil conditions, surrounding atmospheric conditions, and surrounding topography.

11. The plant analysis system of claim 1, further comprising an asset management dashboard for accessing, viewing, analyzing and controlling a library of plant records.

12. The plant analysis system of claim 11, wherein said asset management dashboard integrates spatial information of a subset of said plant records in a configurable display, said subset of said plant records correspond to a plot on an orchard, and wherein said asset management dashboard allows users to generate counting and statistical reports about said plant records.

13. The plant analysis system of claim 11, wherein the processor is further configured to create a record of said plant in a library of plant records, and the record of said plant associates said plant with said spectral signature, said plant color, said spectral data, said assembled point cloud data, and said morphological data.

14. A method for analyzing a plant, comprising:
measure, using a data acquisition component coupled to a transport vehicle, properties of a plant utilizing waveform light detection and ranging (LiDAR) to assemble point cloud data, wherein said point cloud data comprises a plurality of three dimensional vertices each of which represents an external surface associated with said plant;
collect, using the data acquisition component, photographic data of said plant;
collect, using the data acquisition component, spectral data for said plant;
geo-register the point cloud data and photographic data;
associate a plurality of said three dimensional vertices of said point cloud data with global positioning satellite (GPS) data, said photographic data, and said spectral data;
determine, using one or more processors, a spectral signature of said plant based on said spectral data;
determine, using the one or more processors, plant color based on said photographic data;
associate said point cloud data with said plant color; and
generate, using the one or more processors, morphological data of said plant based on said point cloud data, said morphological data comprising one or more of plant stem diameter, plant height, plant volume, and plant leaf density.

15. The method of claim 14, wherein:
said morphological data is generated by segmenting said point cloud data to identify boundaries of said plant; or
said morphological data is classified to identify a plant feature, said plant feature comprising a branching structure, trunk, biomass, canopy, fruit, blossom, fruit cluster, or blossom cluster.

16. The method of claim 14, wherein said point cloud data and said plant color is utilized to discriminate a fruit, blossom, fruit cluster, or blossom cluster from a shadow based, at least in part, on analyzing a variation of said plant color and a geometric shape defined by the three dimensional vertices of said point cloud data.

17. The method of claim 14, further comprising:
measuring atmospheric conditions; and
determining a phenotype of the plant based on said spectral signature, said morphological data, and said atmospheric conditions.

18. The method of claim 14, further comprising:
determining a number and a size of fruits or blossoms on the plant based one or more of said point cloud data or said plant color data, wherein said number and size of fruits or blossoms on the plant is determined by clustering said point cloud data and plant color data, and a crop yield is estimated based, at least in part, on said number and size of fruits or blossoms on the plant.

19. The method of claim 14, wherein:
the spectral signature of the plant is compared with a second spectral signature from a library of plant records to:
  detect a presence of a plant disease based on said comparison of the spectral signature with the second spectral signature; or
  detect a presence of wilt or leaf drop caused by environmental stressors based on said comparison of the spectral signature with the second spectral signature.

20. The method of claim 14, further comprising:
creating a record of said plant in a library of plant records, wherein the record of said plant associates said plant with said spectral signature, said plant color, said spectral data, said assembled point cloud data, and said morphological data.

* * * * *